United States Patent
Wiley et al.

(10) Patent No.: US 7,265,121 B2
(45) Date of Patent: Sep. 4, 2007

(54) CHEMICAL COMPOUNDS

(75) Inventors: Michael Robert Wiley, Indianapolis, IN (US); Daniel Jon Sall, Greenwood, IN (US); John Walter Liebeschuetz, Bollington (GB)

(73) Assignee: Eli Lilly and Company, Indianapolis, IN (US)

( * ) Notice: Subject to any disclaimer, the term of this patent is extended or adjusted under 35 U.S.C. 154(b) by 125 days.

(21) Appl. No.: 10/483,264

(22) PCT Filed: Jul. 24, 2002

(86) PCT No.: PCT/US02/21292

§ 371 (c)(1), (2), (4) Date: Jan. 15, 2004

(87) PCT Pub. No.: WO03/010160

PCT Pub. Date: Feb. 6, 2003

(65) Prior Publication Data

US 2005/0026928 A1 Feb. 3, 2005

Related U.S. Application Data

(60) Provisional application No. 60/339,317, filed on Dec. 12, 2001, provisional application No. 60/311,462, filed on Aug. 13, 2001, provisional application No. 60/307,634, filed on Jul. 26, 2001.

(51) Int. Cl.
*A61K 31/495* (2006.01)
*C07D 401/04* (2006.01)

(52) U.S. Cl. ............... 514/252.13; 514/255.05; 544/129

(58) Field of Classification Search ........... 514/252.14, 514/255, 252.13, 255.05; 544/129
See application file for complete search history.

(56) References Cited

U.S. PATENT DOCUMENTS 6,566,373 B2 * 5/2003 Gribble et al. ............ 514/314
6,936,611 B2 * 8/2005 Liebeschuetz et al. . 514/252.14

FOREIGN PATENT DOCUMENTS

| WO | WO95/34311 | 12/1995 |
|---|---|---|
| WO | WO99/11657 | 3/1999 |
| WO | WO99/11658 | 3/1999 |
| WO | WO 00/76970 | 12/2000 |
| WO | WO 00/76971 | 12/2000 |
| WO | WO 01/96296 | 12/2001 |
| WO | WO 01/96303 | 12/2001 |
| WO | WO 01/96304 | 12/2001 |
| WO | WO 01/96323 | 12/2001 |
| WO | WO 02/16312 | 2/2002 |
| WO | WO 02/100847 | 12/2002 |

OTHER PUBLICATIONS

Lu et al. "Preparation of quinolyl amide derivatives as CCR-5 antagonists" CA 142:93694 (2004).*
Gribble et al. "Preparation of heterocyclyl . . . " CA 130:142262 (1998).*
Gans et al. "preparing modular laveling . . . " Drug information J. v.30, pp. 769-783 (1996).*
Bureua circular "Revised checklist of requirments . . . " Repulic of the Phillipines (1997).*
"The library of european union pharmaceutical indicators" Euro-Med-Stat (2004).*
Kabana Skin Care (2006) p. 1-4.*
Jones, S D, et al., Bioorg. Med. Chem. Lett., vol. 11, 2001, pp. 733-736.

* cited by examiner

*Primary Examiner*—Celia Chang
(74) *Attorney, Agent, or Firm*—Thomas E. Jackson

(57) ABSTRACT

Compounds of formula (I)

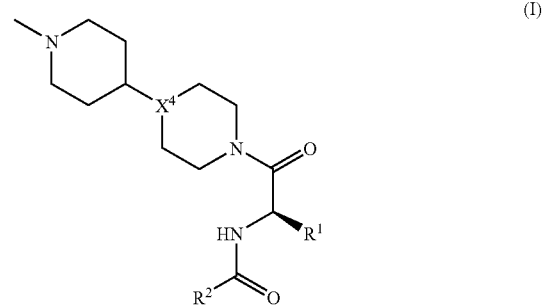

in which $R^1$, $R^2$ and $X^4$ have the meanings given in the specification are Factor Xa inhibitors useful in the treatment of thrombotic disorders.

17 Claims, No Drawings

CHEMICAL COMPOUNDS

This application claims the benefit of U.S. Provisional Applications No. 60/307,634, filed Jul. 26, 2001; 60/311,462, filed Aug. 13, 2001; and 60/339,317, filed Dec. 12, 2001, each of which is incorporated by reference herein.

The present invention relates to compounds useful as pharmaceuticals, to pharmaceutical compositions comprising the compounds, to a process for preparing the compounds, to intermediates useful in the preparation of the compounds, and to use of the compounds as pharmaceuticals.

Cardiovascular disease continues to present a major worldwide health problem, and is a common cause of serious illness and death.

One line of investigation being pursued by researchers in the search for new treatments for cardiovascular disease is based upon the hypothesis that an inhibitor of the serine protease, Factor Xa, may be useful as an anticoagulant agent in the treatment of thrombotic disease.

Inhibitors of Factor Xa are known. For example, WO 99/11657, WO 99/11658 and WO 00/76971 disclose certain compounds containing an aromatic group, a glycine residue that bears a cyclic group and a lipophilic group. WO 99/11657, which discloses compounds in which the aromatic group is an aminoisoquinoline group, also generically discloses aminoisoquinoline compounds containing a glycine residue that bears an acyclic group.

Surprisingly, compounds containing particular phenyl or indolyl groups, a glycine residue bearing an alkyl group and a 4-(1-methylpiperidin-4-yl)piperidin-1-yl or 4-(1-methylpiperidin-4-yl)piperazin-1-yl group have now been found that are selective Factor Xa inhibitors and have particularly advantageous properties.

Accordingly, the present invention provides a compound of formula (I)

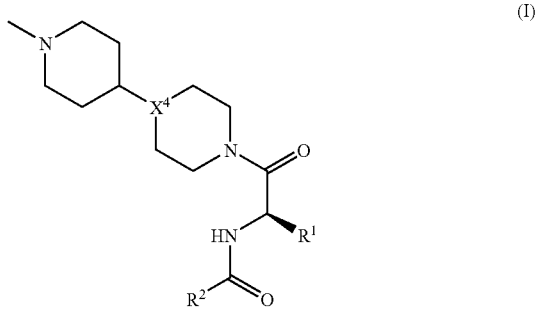

(I)

in which $R^1$ represents (1-4C)alkyl, (2-4C)alkenyl or (2-4C)alkynyl; and $R^2$ is selected from

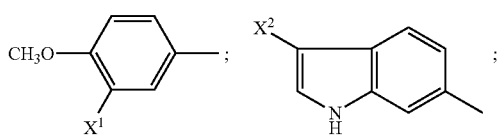

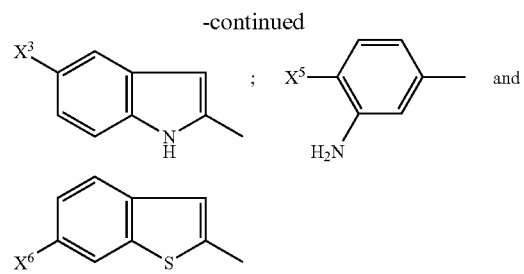

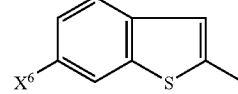

in which $X^1$ represents a hydrogen atom or a halogen atom;

$X^2$ represents a hydrogen atom, a methyl group, a chlorine atom or a bromine atom;

$X^3$ represents a hydrogen atom, a methyl group or a halogen atom;

$X^5$ represents chloro, methoxy or methyl;

$X^6$ represents a hydrogen atom, a halogen atom or a methyl group; and $X^4$ represents CH or N;

or a pharmaceutically acceptable salt thereof.

Compounds of formula (I) have been found to be potent and selective inhibitors of the serine protease, Factor Xa, to have good anticoagulant activity in human plasma, to have good plasma exposure upon oral administration to mammals, and to possess particularly advantageous pharmacological and toxicological profiles of activity.

In one group of compounds of formula (I), the group $R^2$ is selected from

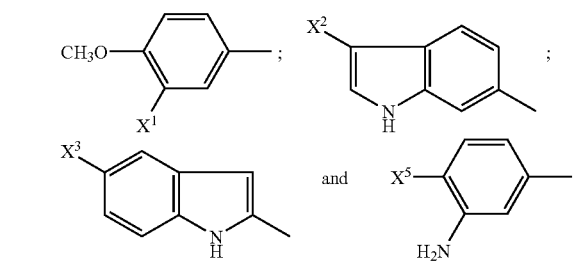

In another group of compounds of formula (I), the group $R^2$ is selected from

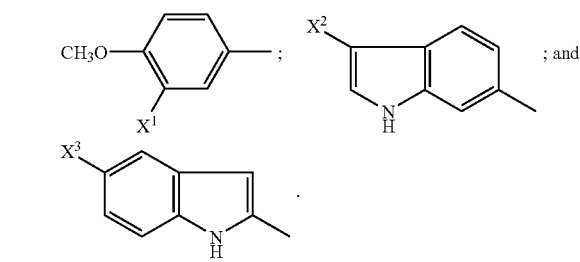

In yet another group of compounds of formula (I), the group $R^2$ is selected from

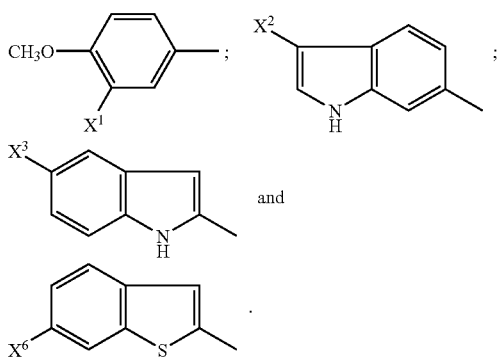

$R^1$ is preferably a (1-4C)alkyl group.

Examples of particular values for $R^1$ are methyl, ethyl, propyl, 2-propyl, butyl, t-butyl, 1-methylpropyl and 2-methylpropyl. Further examples are prop-3-enyl and prop-3-ynyl. When $R^1$ is 1-methylpropyl, the preferred stereochemistry is that corresponding to (D)-isoleucine.

Preferably, $R^1$ is 2-propyl.

$X^1$ preferably represents a hydrogen atom or a fluorine atom.

$X^2$ preferably represents a hydrogen atom or a chlorine atom.

$X^3$ preferably represents a fluorine or chlorine atom, such as a chlorine atom.

$X^6$ preferably represents a chlorine atom.

Examples of particular values for $R^2$ are 4-methoxyphenyl, indol-6-yl, 3-methylindol-6-yl, 3-chloroindol-6-yl and 5-chloroindol-2-yl. Further examples are 3-fluoro-4-methoxyphenyl, 5-fluoroindol-2-yl and 6-chlorobenzo[b]thiophen-2-yl. Particular mention may be made of compounds of formula (I) in which $R^2$ is 3-fluoro-4-methoxyphenyl and of compounds of formula (I) in which $R^2$ is 5-fluoroindol-2-yl.

$R^2$ is preferably 4-methoxyphenyl, indol-6-yl or 5-chloroindol-2-yl.

One particular value for $X^4$ is CH.

When $X^4$ represents CH, especially preferred compounds of formula (I) are:—
1-(4-methoxybenzoyl-D-valinyl)-4-(1-methylpiperidin-4-yl)-piperidine and
1-(indole-6-carbonyl-D-valinyl)-4-(1-methylpiperidin-4-yl)piperidine;
and pharmaceutically acceptable salts thereof, particularly the methanesulfonic acid salt of the former.

Another particular value for $X^4$ is N.

When $X^4$ represents N, an especially preferred compound of formula (I) is:—
1-(5-chloroindole-2-carbonyl-D-valinyl)-4-(1-methyl-piperidin-4-yl)piperazine,
and pharmaceutically acceptable salts thereof.

Examples of compounds of formula (I) in which $R^2$ represents

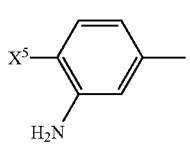

are:
1-(3-amino-4-chlorobenzoyl-D-valinyl)-4-(1-methylpiperidin-4-yl)piperidine;
1-(3-amino-4-chlorobenzoyl-D-valinyl)-4-(1-methylpiperidin-4-yl)piperazine;
1-(3-amino-4-methoxybenzoyl-D-valinyl)-4-(1-methylpiperidin-4-yl)piperidine;
1-(3-amino-4-methoxybenzoyl-D-valinyl)-4-(1-methylpiperidin-4-yl)piperazine;
1-(3-amino-4-methylbenzoyl-D-valinyl)-4-(1-methylpiperidin-4-yl)piperidine;
1-(3-amino-4-methylbenzoyl-D-valinyl)-4-(1-methylpiperidin-4-yl)piperazine;

and pharmaceutically acceptable salts thereof.

It will be appreciated that the compounds of formula (I) contain a center of asymmetry that has the (D) configuration. This is the conformation that would result from construction from a D-α-amino acid $H_2N—CH(R^1)COOH$. The compounds may therefore exist and be isolated in a mixture with the corresponding (L) isomer, such as a racemic mixture, or separately. Preferably the compounds are isolated substantially free of the (L) isomer.

It will also be appreciated that the compounds of formula (I) or their pharmaceutically acceptable salts may be isolated in the form of a solvate, and accordingly that any such solvate is included within the scope of the present invention.

In the compounds according to the invention, unless otherwise indicated, examples of the term "halogen atom" are fluoro and chloro. The specific name of an alkyl group, such as propyl or butyl, signifies the unbranched or n-isomer, unless otherwise indicated.

The compounds of formula (I) and their pharmaceutically acceptable salts may be prepared by a process, which comprises:

(a) reacting a compound of formula (II)

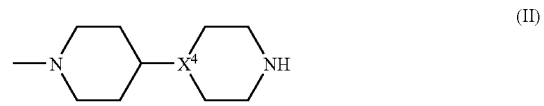

or a salt thereof, with a compound of formula (III)

or a reactive derivative thereof; or (b) reacting a compound of formula (IV)

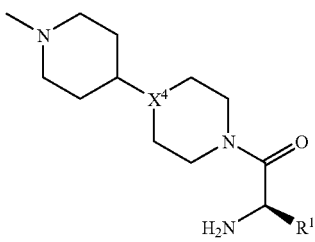

(IV)

or a salt thereof, with a compound of formula (V)

HOOC—R² (V)

or a reactive derivative thereof;

followed, if a pharmaceutically acceptable salt is desired, by forming a pharmaceutically acceptable salt.

The reaction between a compound of formula (II) with a compound of formula (III) may conveniently be performed employing reagents and reaction conditions conventionally used for the formation of an amide bond. The reaction is conveniently carried out in the presence of a benzotriazole-based reagent such as 1-hydroxybenzotriazole or 1-hydroxy-7-azabenzotriazole and a dehydrating agent such as dicyclohexyl-carbodiimide or 1-(3-dimethylaminopropyl)-3-ethylcarbodiimide, in an inert organic solvent such as dimethylformamide and/or methylene chloride. The reaction is conveniently conducted at a temperature of from 0 to 50° C., preferably at ambient temperature. If a salt of a compound of formula (II) is used, the reaction is conveniently performed in the additional presence of a base such as triethylamine. Other suitable reagents and solvents are known in the art, for example an acid halide, such as the chloride in the presence of a base, such as triethylamine.

The reaction between a compound of formula (IV) with a compound of formula (V) may conveniently be performed employing reagents and reaction conditions conventionally used for the formation of an amide bond. The reaction is conveniently carried out in the presence of a benzotriazole-based reagent such as 1-hydroxybenzotriazole or 1-hydroxy-7-azabenzotriazole and a dehydrating agent such as dicyclohexylcarbodiimide or 1-(3-dimethylaminopropyl)-3-ethylcarbodiimide, in an inert organic solvent such as dimethylformamide and/or methylene chloride. The reaction is conveniently conducted at a temperature of from 0 to 50° C., preferably at ambient temperature. If a salt of a compound of formula (IV) is used, the reaction is conveniently performed in the additional presence of a base such as triethylamine. Other suitable reagents and solvents are known in the art, for example an acid halide, such as p-anisoyl chloride in the presence of a base, such as triethylamine. Alternatively, the compound of formula (IV) may be reacted with a compound of formula (V) in the presence of diethyl cyanophosphonate. This reaction is conveniently performed in an organic solvent such as dichloromethane in the presence of a base, such as triethylamine. The temperature is conveniently in the range of from −25 to 25° C.

The compound of formula (II) in which $X^4$ is CH is known, for example from WO 00/76971 at pages 163-164, and is named as 4-(1-methylpiperidin-4-yl)piperidine or 1-methyl-4,4'-bispiperidine. The compound of formula (II) in which $X^4$ is N is commercially available. It is referred to herein as 4-(1-methylpiperidin-4-yl)piperazine, but also may be named 1-(1-methylpiperidin-4-yl)piperazine.

The compounds of formula (III) may be prepared by reacting a compound of formula (VI)

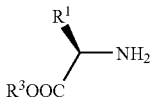

(VI)

in which $R^3$ represents a carboxyl protecting group, for example a (1-6C)alkyl group, such as methyl or ethyl, with a compound of formula (IV) to afford a compound of formula (VII)

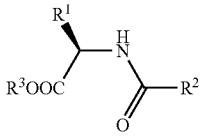

(VII)

followed by removing the protecting group.

The compounds of formula (IV) may be prepared by reacting a compound of formula (II) with a compound of formula (VIII)

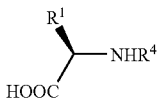

(VIII)

in which $R^4$ represents an amino protecting group, such as t-butoxycarbonyl (Boc) to afford a compound of formula (IX)

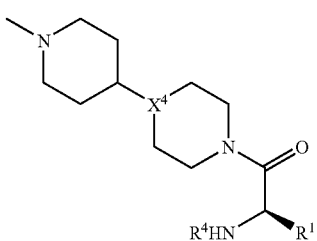

(IX)

followed by removing the protecting group.

The compounds of formulae (VI) and (VIII) are known or may be prepared using conventional methods for the preparation of amino acids protected on the carboxy or amino group.

The compounds of formula (V) are well known.

The protection of amino and carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$-$C_6$ alkyl groups such as methyl, ethyl, t-butyl and t-amyl; aryl($C_1$-$C_4$)alkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups include acyl groups, such as groups of formula RCO in which R represents $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$-$C_4$ alkyl and $C_1$-$C_4$ alkoxy.

Preferred amino protecting groups include benzyloxycarbonyl (Cbz) and t-butoxycarbonyl (Boc).

Certain of the intermediates described herein, for example the compounds of formulae (III) and (IV), are believed to be novel and accordingly are provided as further aspects of the invention.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Viewed from this aspect the invention provides a pharmaceutical composition, which comprises the compound of formula (I) or a pharmaceutically acceptable salt thereof, together with a pharmaceutically acceptable diluent or carrier.

According to another aspect, the present invention provides a compound of formula (I) or a pharmaceutically acceptable salt thereof, for use in therapy.

According to another aspect, the present invention provides the use of a compound of formula (I) or a pharmaceutically acceptable salt thereof, for the manufacture of a medicament for the treatment of a thrombotic disorder.

According to another aspect, the present invention provides a method of treating a thrombotic disorder in a subject requiring treatment, which comprises administering an effective amount of a compound of formula (I) or a pharmaceutically acceptable salt thereof.

The subject may be a human or a non-human animal, such as a non-human mammal, for example a cat, dog, horse, cow or sheep.

The thrombotic disorder may be, for example, venous thrombosis, pulmonary embolism, arterial thrombosis, myocardial ischaemia, myocardial infarction or cerebral thrombosis. A particular indication is, for example, prophylaxis of post-operative venous thrombosis following high risk orthopedic surgery (such as hip or knee replacement), primary treatment of venous thrombosis, secondary prevention of ischemic cardiovascular complications following myocardial infarction (in combination with e.g. low dose aspirin), or prevention of embolic stroke in non-valvular atrial fibrillation. The compounds may also be used in accordance with the method of the invention in the treatment of acute vessel closure associated with thrombolytic therapy and restenosis, for example after transluminal coronary angioplasty or bypass grafting of the coronary or peripheral arteries, and in the maintenance of vascular access patency in long term hemodialysis patients.

The dosage of the compound of formula (I) will depend upon the nature and severity of the condition being treated, the administration route and the size and species of the subject. In general, quantities in the range of from 0.01 to 100 µM/kg bodyweight will be administered.

As used herein, the term "treatment" includes prophylactic use. The term "effective amount" refers to the amount of the compound of formula (I) that is effective to reduce or inhibit the development of the symptoms of the thrombotic disorder being treated.

The compound according to the invention may be administered alone or in combination with an anticoagulant having a different mode of action or with a thrombolytic agent.

The following Examples illustrate the invention.

Abbreviations used follow IUPAC-IUB nomenclature. Additional abbreviations are Boc, tertiary-butyloxycarbonyl; DCC, dicyclohexylcarbodiimide; DIEA, N,N-diisopropylethylamine; DMSO, dimethyl sulfoxide (perdeuterated if for NMR); DMF, dimethylformamide; EDCI, 1-(3-dimethylaminopropyl)-3-ethylcarbodiimide hydrochloride; ES-MS, electrospray mass spectrum; EtOAc, ethyl acetate; $Et_2O$, diethyl ether; HOAt, 1-hydroxy-7-azabenzotriazole; HOBt, 1-hydroxy benzotriazole; HPLC, high pressure liquid chromatography; MeOH, methanol; SCX, strong cation exchange; TEA, triethylamine; TFA, trifluoroacetic acid; and THF, tetrahydrofuran. Reagents were obtained from a variety of commercial sources.

General Coupling Methods

Method 1: A solution or suspension of an amine or amine hydrochloride salt (1 molar equivalent, approximately 0.2 M) in THF, dichloromethane, or DMF (or a mixture of any of these solvents) is treated with a carboxylic acid (approximately 1 molar equivalent), either HOBt or HOAt (approximately 1 molar equivalent), either TEA or DIEA (0-3 molar equivalent), and either EDCI or DCC (approximately 1 molar equivalent). After stirring overnight at room temperature, the solvents are removed and the residue is diluted with ethyl acetate or dichloromethane and washed with saturated aqueous sodium bicarbonate. The organic solution is then dried with $MgSO_4$, filtered and concentrated in vacuo. If necessary, the product is purified by chromatography over silica gel, eluting with a gradient of 0% through 2 to 12% (2 N ammonia/methanol) in dichloromethane or chloroform. The product-containing fractions are then combined and concentrated in vacuo.

Method 2: To a stirring solution of an amine or amine hydrochloride salt (1 molar equivalent), triethylamine (1-3 molar equivalent), and a carboxylic acid (about 1.2 molar equivalent) in dichloromethane (0.2-0.5 M) at 0° C., is slowly added diethyl cyanophosphonate (about 1.2 molar equivalent). After stirring overnight, the solvents are removed in vacuo; and the residue is partitioned between water and an organic solvent, such as ethyl acetate or dichloromethane, and washed with saturated aqueous $NaHCO_3$, followed by brine. The organic phase is then dried with $MgSO_4$ or $Na_2SO_4$, filtered and concentrated in vacuo. If necessary, the product is purified by chromatography over silica gel, eluting with a gradient of 0-10% (2 N ammonia/methanol) in either dichloromethane or chloroform. The product-containing fractions are then combined and concentrated in vacuo.

Method 3: The amine or amine hydrochloride salt (1 molar equivalent) and triethylamine (1-3 molar equivalent) are dissolved in dichloromethane (0.2-0.5 M) and an acid chloride (about 1.2 molar equivalent) is added. After stirring for about 3 h, the volatiles are removed in vacuo; and the residue is dissolved in methanol (possibly with an organic cosolvent such as dichloromethane) and loaded onto a strong cation exchange (SCX) column. The column is washed with methanol, and then the desired product is eluted from the column with a solution of ammonia or triethylamine in methanol (possibly with an organic cosolvent such as dichloromethane). The product containing fractions are then combined and concentrated in vacuo. If necessary, the product can be purified further by chromatography over silica gel, eluting with a gradient of 0-10% (2 N ammonia/methanol) in either dichloromethane or chloroform. The product-containing fractions are then combined and concentrated in vacuo.

General Deprotection Methods

Method 1: A solution of the t-butyl carbamate (1 molar equivalent) in $CH_2Cl_2$ (0.2 M) is treated with anisole (5 eq) and TFA (20% by volume). After stirring 1 to 3 h at ambient temperature, the reaction mixture is concentrated in vacuo. The crude residue (TFA salt) is purified by strong cation exchange chromatography (SCX). The SCX column is washed with a 5% solution of acetic acid in methanol, and the TFA salt is dissolved in methanol (possibly with a cosolvent such as dichloromethane) and loaded onto the SCX column. The column is then washed with methanol (possibly with a cosolvent such as dichloromethane) and then the free base is eluted from the column with a 2 N solution of ammonia or triethylamine in methanol (possibly with a cosolvent such as dichloromethane). The product containing fractions are then combined and concentrated in vacuo to give the product in the free base form.

Method 2: HCl gas is bubbled into a solution of the t-butylcarbamate in anhydrous MeOH (0.1 M) for approximately 10 to 30 min; then the reaction mixture is concentrated in vacuo to give a hydrochloride salt of the title amine.

General HCl Salt Formation Methods

Method 1: The free base is dissolved in 0.2 N aqueous HCl (1-2 equivalents of HCl). The resulting solution is freeze-dried to give the amine hydrochloride salt.

Method 2: A solution of the free base in a small amount of $CH_2Cl_2$ is treated with 1.0-2.2 equivalents of 1 M HCl in ether. After stirring 30 min, the reaction mixture is filtered, and the resulting solid is rinsed with ether and dried to give the amine hydrochloride salt.

General Analytical HPLC Methods

Method 1: Vydac C18 (4.6×250 mm column), elute with a linear gradient of 90/10 through 50/50 (0.1% TFA in water/0.1% TFA in acetonitrile) over 40 min, 1 mL/min, $\lambda$=214 nm.

Method 2: Xterra RP18 (4.6×50 mm column), gradient of 2-50% $CH_3CN$ in $H_2O$ with 0.1% TFA, 1 mL/min, over 30 min, $\lambda$=214 nm.

Method 3: Xterra RP18 (4.6×150 mm column), gradient of 10-50% $CH_3CN$ in $H_2O$ with 0.1% TFA, 1 mL/min, over 40 min, Waters 996 PDA and/or Sedex ELS detection.

Preparation of Intermediates 1-(Boc-D-alaninyl)-4-(1-methylpiperidin-4-yl)piperidine.

Prepared from Boc-D-alanine and 4-(1-methylpiperidin-4-yl)piperidine dihydrobromide using methods substantially equivalent to General Coupling Method 1.
$^1$H NMR.
ES-MS, m/z 354.3 $(M+1)^+$.
Analysis for $C_{19}H_{35}N_3O_3 \cdot 0.3H_2O$: Calcd: C, 63.58; H, 10.00; N, 11.71. Found: C, 63.46; H, 9.82; N, 11.61.

1-(Boc-D-ethylglycinyl)-4-(1-methylpiperidin-4-yl)piperidine

Prepared from Boc-D-ethylglycine and 4-(1-methylpiperidin-4-yl)piperidine dihydrobromide using methods substantially equivalent to General Coupling Method 1.
$^1$H NMR.
ES-MS, m/z 368.3 $(M+1)^+$.
Analysis for $C_{20}H_{37}N_3O_3 \cdot 0.2H_2O$: Calcd: C, 64.72; H, 10.16; N, 11.32. Found: C, 65.03; H, 9.98; N, 10.94.

1-[Boc-D-(propyl)glycinyl]-4-(1-methylpiperidin-4-yl)-piperidine

Prepared from Boc-D-(propyl)glycine and 4-(1-methylpiperidin-4-yl)piperidine dihydrobromide using methods substantially equivalent to General Coupling Method 1.
$^1$H NMR.
ES-MS, m/z 382.3$(M+1)^+$.
Analysis for $C_{21}H_{39}N_3O_3 \cdot 1.3H_2O$: Calcd: C 62.28; H 10.35; N 10.38. Found: C 62.29; H 9.77; N 10.01.

1-[Boc-D-(butyl)glycinyl]-4-(1-methylpiperidin-4-yl)piperidine

Prepared from Boc-D-(n-butyl)glycine and 4-(1-methylpiperidin-4-yl)piperidine dihydrobromide using methods substantially equivalent to General Coupling Method 1.
$^1$H NMR.
ES-MS, m/z 396.3$(M+1)^+$.
Analysis for $C_{22}H_{41}N_3O_3$: Calcd: C, 66.80; H, 10.45; N, 10.62. Found: C, 66.68; H, 10.41; N, 10.50.

1-(Boc-D-Valinyl)-4-(1-methylpiperidin-4-yl)piperidine

To a solution of Boc-D-Val-OH (33.0 g, 152 mmol) in anhydrous DMF (1.5 L) is added 4-(1-methylpiperidin-4-yl)-piperidine dihydrobromide (52.2 g, 152 mmol) [4-(1-methyl-piperidin-4-yl)piperidine dihydrobromide is also named 1-methyl-4,4'-bispiperidine dihydrobromide; and its preparation is described in WO 00/76971 at pages 163-164.] followed by triethylamine (63.5 mL, 456 mmol), HOBt (20.5 g, 152 mmol) and DCC (31.3 g, 152 mmol) at room temperature. The reaction is allowed to stir at room temperature overnight. The mixture is then poured into aqueous LiCl (1.5 L) and extracted with $CH_2Cl_2$ (3×2 L). The organic layers are combined, dried over $Na_2SO_4$, filtered and concentrated in vacuo. The residue is dissolved in $CHCl_3$ (1 L), filtered and concentrated in vacuo. The crude material is purified using chromatography over silica gel, eluting with 4% (2 M NH$_3$ in MeOH)/CHCl$_3$ to give 43.3 g (75%) of the title compound as a tan foam.

$^1$H NMR (DMSO-d$_6$) δ 6.68 (m, 1H), 4.42 (m, 1H), 4.19 (m, 1H), 2.94 (m, 1H), 2.76 (m, 2H), 2.47 (m, 1H), 2.11 (s, 3H), 1.89 (bs, 1H), 1.8-1.5 (bm, 6H), 1.37 (s, 9H), 1.2-0.9 (bm, 7H), 0.82 (m, 6H).

ES-MS, m/z 382.3 (M+1)$^+$.

1-(Boc-D-leucinyl)-4-(1-methylpiperidin-4-yl)piperidine

Prepared from Boc-D-leucine and 4-(1-methylpiperidin-4-yl)piperidine dihydrobromide using methods substantially equivalent to General Coupling Method 1.

ES-MS, m/z 396.4(M+1)$^+$.

1-[Boc-D-(t-butyl)glycinyl]-4-(1-methylpiperidin-4-yl)-piperidine

Prepared from Boc-D-(t-butyl)glycine and 4-(1-methylpiperidin-4-yl)piperidine dihydrobromide using methods substantially equivalent to General Coupling Method 1.

$^1$H NMR.

ES-MS, m/z 396.3(M+1)$^+$.

Analysis for C$_{22}$H$_{41}$N$_3$O$_3$·1.3H$_2$O: Calcd: C, 64.73; H, 10.47; N, 10.29. Found: C, 64.65; H, 10.03; N, 10.30.

1-(Boc-D-valinyl)-4-(1-methylpiperidin-4-yl)piperazine

To a stirring solution of Boc-D-valine (5.0 g, 23 mmol) in dichloromethane (230 mL) is added HOBt (3.42 g, 25.3 mmol), followed by EDCI (4.85 g, 25.3 mmol), followed by 4-(1-methylpiperidin-4-yl)piperazine (4.2 g, 23 mmol). After stirring overnight, the solution is washed with saturated aqueous NaHCO$_3$, followed by brine, and then concentrated in vacuo. The residue is chromatographed over silica gel, eluting with a gradient of 0-10% (2 N ammonia/methanol) in chloroform. The product-containing fractions are combined and concentrated in vacuo to give the title product (8.98 g, quantitative) as an off-white solid.

$^1$H NMR.

ES-MS, m/z 383.3(M+1)$^+$.

Analysis for C$_{22}$H$_{41}$N$_3$O$_3$·0.5H$_2$O: Calcd: C, 61.35; H, 10.04; N, 14.31. Found: C, 61.50; H, 9.68; N, 14.29.

1-[Boc-D-(t-butyl)glycinyl]-4-(1-methylpiperidin-4-yl)-piperazine

Prepared from Boc-D-(t-butyl)glycine and 4-(1-methyl-piperidin-4-yl)piperazine using methods substantially equivalent to General Coupling Method 1.

$^1$H NMR.

ES-MS, m/z 397.3(M+1)$^+$.

Analysis for C$_{21}$H$_{40}$N$_4$O$_3$·0.5H$_2$O: Calcd: C, 62.19; H, 10.1; N, 13.81. Found: C, 62.08; H, 9.89; N, 13.88.

1-(Boc-D-isoleucinyl)-4-(1-methylpiperidin-4-yl)piperazine

Prepared from Boc-D-isoleucine and 4-(1-methyl-piperidin-4-yl)piperazine using methods substantially equivalent to General Coupling Method 1.

$^1$H NMR.

ES-MS, m/z 397.4 (M+1)$^+$.

Analysis for C$_{21}$H$_{40}$N$_4$O$_3$ 0.2H$_2$O·0.2CH$_2$Cl$_2$: Calcd: C, 61.04; H, 9.86; N, 13.43. Found: C, 60.87; H, 9.53; N, 13.60.

1-(Boc-D-leucinyl)-4-(1-methylpiperidin-4-yl)piperazine

Prepared from Boc-D-leucine and 4-(1-methylpiperidin-4-yl)piperazine using methods substantially equivalent to General Coupling Method 1.

ES-MS, m/z 397.3 (M+1)$^+$.

1-D-Alaninyl-4-(1-methylpiperidin-4-yl)piperidine

Prepared from 1-(Boc-D-alaninyl)-4-(1-methylpiperidin-4-yl)piperidine using methods substantially equivalent to those described in General Deprotection Method 1.

$^1$H NMR.

ES-MS, m/z 254.2 (M+1)$^+$.

1-D-Ethylglycinyl-4-(1-methylpiperidin-4-yl)piperidine hydrochloride

Prepared from 1-(Boc-D-ethylglycinyl)-4-(1-methyl-piperidin-4-yl)piperidine using methods substantially equivalent to those described in General Deprotection Method 2.

$^1$H NMR.

ES-MS, m/z 268.2 (M+1)$^+$.

Analysis for C$_{15}$H$_{29}$N$_3$O·2.7 HCl·0.6H$_2$O: Calcd: C, 47.60; H, 8.82; N, 11.10. Found: C, 47.59; H, 8.82; N, 10.97.

1-D-(Propyl)glycinyl-4-(1-methylpiperidin-4-yl)piperidine hydrochloride

Prepared from 1-[Boc-D-(propyl)glycinyl]-4-(1-methyl-piperidin-4-yl)piperidine using methods substantially equivalent to those described in General Deprotection Method 2.

$^1$H NMR.

ES-MS, m/z 282.3 (M+1)$^+$.

Analysis for C$_{16}$H$_{31}$N$_3$O·2.6 HCl·1.6H$_2$O: Calcd: C, 47.44; H, 9.16; N, 10.37. Found: C, 47.35; H, 9.18; N, 10.29.

1-D-(Butyl)glycinyl-4-(1-methylpiperidin-4-yl)piperidine hydrochloride

Prepared from 1-[Boc-D-(butyl)glycinyl-4-(1-methyl-piperidin-4-yl)piperidine using methods substantially equivalent to those described in General Deprotection Method 2.

$^1$H NMR.

ES-MS, m/z 296.3 (M+1)$^+$.

Analysis for C$_{17}$H$_{33}$N$_3$O·2.6HCl·1.6H$_2$O: Calcd: C, 51.61; H, 9.30; N, 10.62; Found: C, 51.59; H, 9.27; N, 10.51.

1-D-Valinyl-4-(1-methylpiperidin-4-yl)piperidine Dihydrochloride 1-(Boc-D-Valinyl)-4-(1-methylpiperidin-4-yl)piperidine (23.3 g, 61.1 mmol) is dissolved in anhydrous methanol (700 mL), cooled to 0° C. and treated with HCl (gas) until HPLC indicates consumption of starting material is complete. The solvent is removed in vacuo to give 20.8 g (96%) of the title compound as an off-white foam.

$^1$H NMR (DMSO-d$_6$) δ 11.8 (bs, 1H), 8.19 (m, 3H), 4.77 (bs, 3H), 4.44 (m, 1H), 4.22 (m, 1H), 3.99 (m, 1H), 3.1-2.6 (bm, 6H), 2.01 (m, 1H), 1.9-1.5 (bm, 5H), 1.3 (m, 2H), 0.98 (m, 3H), 0.91 (m, 3H).

ES-MS, m/z 282.3 (M+1)$^+$.

1-D-Leucinyl-4-(1-methylpiperidin-4-yl)piperidine

Prepared from 1-(Boc-D-leucinyl)-4-(1-methylpiperidin-4-yl)piperidine using methods substantially equivalent to those described in General Deprotection Method 1.
$^1$H NMR.
ES-MS, m/z 296.2 (M+1)$^+$.

1-D-(t-Butyl)glycinyl-4-(1-methylpiperidin-4-yl) piperidine

Prepared from 1-[Boc-D-(t-butyl)glycinyl]-4-(1-methylpiperidin-4-yl)piperidine using methods substantially equivalent to those described in General Deprotection Method 1.
$^1$H NMR.
ES-MS, m/z 296.2 (M+1)$^+$.

1-D-Valinyl-4-(1-methylpiperidin-4-yl)piperazine Trihydrochloride 1-(Boc-D-valinyl)-4-(1-methylpiperidin-4-yl)piperazine (8.9 g, 23 mmol) is dissolved in methanol (500 mL), and HCl gas is bubbled through the stirring solution for 10-15 min. After cooling to room temperature, diethyl ether (500 mL) is added, and the resulting solid is filtered and dried in vacuo to give 8.59 g (94%) of the title compound.
$^1$H NMR.
ES-MS, m/z 283.3 (M+1)$^+$.
Analysis for $C_{15}H_{30}N_3O \cdot 3.0$ HCl$\cdot 0.3H_2O$: Calcd: C, 45.43; H, 8.53; N, 14.11; Found: C, 45.43; H, 8.25; N, 13.89.

1-D-(t-Butyl)glycinyl-4-(1-methylpiperidin-4-yl) piperazine

Prepared from 1-[Boc-D-(t-butyl)glycinyl]-4-(1-methylpiperidin-4-yl)piperazine using methods substantially equivalent to those described in General Deprotection Method 1.
$^1$H NMR.
ES-MS, m/z 297.2 (M+1)$^+$.

1-D-Isoleucinyl-4-(1-methylpiperidin-4-yl)piperazine

Prepared from 1-(Boc-D-isoleucinyl)-4-(1-methylpiperidin-4-yl)piperazine using methods substantially equivalent to those described in General Deprotection Method 1.
ES-MS, m/z 297.3 (M+1)$^+$.

1-D-Leucinyl-4-(1-methylpiperidin-4-yl)piperazine

Prepared from 1-(Boc-D-leucinyl)-4-(1-methylpiperidin-4-yl)piperazine using methods substantially equivalent to those described in General Deprotection Method 1.
$^1$H NMR.
ES-MS, m/z 297.3 (M+1)$^+$.

EXAMPLE 1

1-(Indole-6-carbonyl-D-alaninyl)-4-(1-methylpiperidin-4-yl)-piperidine hydrochloride Prepared from 1-D-alaninyl-4-(1-methylpiperidin-4-yl)-piperidine and indole-6-carboxylic acid using methods substantially equivalent to General Coupling Method 1. The HCl salt is prepared following General Salt Formation Method 2.
$^1$H NMR.
ES-MS, m/z 397.1(M+1)$^+$; 395.3 (M−1)$^-$.
Analytical HPLC (Method 1): 98%, $t_r$=15.2 min.

EXAMPLE 2

1-(Indole-6-carbonyl-D-ethylglycinyl)-4-(1-methylpiperidin-4-yl)piperidine hydrochloride Prepared from 1-D-(ethyl)glycinyl-4-(1-methylpiperidin-4-yl)piperidine hydrochloride and indole-6-carboxylic acid using methods substantially equivalent to General Coupling Method 1. The HCl salt is prepared following General Salt Formation Method 1.
$^1$H NMR.
ES-MS, m/z 411.2 (M+1)$^+$; 409.2 (M−1)$^-$.
Analysis for $C_{24}H_{34}N_4O_2 \cdot 0.9$ HCl$\cdot 2.0 H_2O$: Calcd: C, 60.13; H, 8.18; N, 11.69; Cl, 6.66. Found: C, 59.97; H, 7.97; N, 11.83; Cl, 6.27.
Analytical HPLC (Method 2): >95%, tr 17.4 min.

EXAMPLE 3

1-[Indole-6-carbonyl-D-(propyl)glycinyl]-4-(1-methylpiperidin-4-yl)piperidine hydrochloride Prepared from 1-D-propylglycinyl-4-(1-methylpiperidin-4-yl)piperidine hydrochloride and indole-6-carboxylic acid using methods substantially equivalent to General Coupling Method 1. The HCl salt is prepared following Salt Formation Method 1.
$^1$H NMR.
ES-MS, m/z 425.2 (M+1)$^+$; 423.2 (M−1)$^-$.
Analysis for $C_{25}H_{36}N_4O_2 \cdot 0.9$ HCl$\cdot 2.0 H_2O$: Calcd: C, 60.85; H, 8.35; N, 11.36; Cl, 6.47; Found: C, 60.95; H, 7.98; N, 11.39; Cl, 5.93.
Analytical HPLC (Method 2): >98%, $t_r$=19.1 min.

EXAMPLE 4

1-[Indole-6-carbonyl-D-(butyl)glycinyl]-4-(1-methylpiperidin-4-yl)piperidine hydrochloride Prepared from 1-D-(butyl)glycinyl-4-(1-methylpiperidin-4-yl)piperidine hydrochloride and indole-6-carboxylic acid using methods substantially equivalent to General Coupling Method 1. The HCl salt is prepared following General Salt Formation Method 1.
$^1$H NMR.
ES-MS, m/z 439.2 (M+1)$^+$; 437.2 (M−1)$^-$.
Analysis for $C_{26}H_{38}N_4O_2 \cdot 1$HCl$\cdot 2.2 H_2O$: Calcd: C, 60.67; H, 8.50; N, 10.89; Cl, 6.89. Found: C, 60.53; H, 8.13; N, 10.96; Cl, 6.67.
Analytical HPLC (Method 2): >95%, $t_r$=21.1 min.

EXAMPLE 5

1-(4-Methoxybenzoyl-D-valinyl)-4-(1-methylpiperidin-4-yl)-piperidine

1-D-Valinyl-4-(1-methylpiperidin-4-yl)piperidine dihydrochloride (15.6 g, 44.1 mmol) is slurried in anhydrous CH$_2$Cl$_2$ (400 mL); and to the slurry is added triethylamine (19.7 mL, 141.0 mmol), followed by p-anisoyl chloride (7.9 mL, 52.9 mmol). The reaction is allowed to stir for about 30 min and then quenched with the addition of saturated NaHCO$_3$ (300 mL), followed by the separation of the phases. The organic layer is washed with saturated NaHCO$_3$ (2×300 mL), dried over Na$_2$SO$_4$, filtered and concentrated in vacuo. The residue is purified by chromatography over silica gel, eluting with 2.5% (2 M NH$_3$ in MeOH)/CHCl$_3$ to give 16.3 g (89%) of the title compound as a white foam.

$^1$H NMR (DMSO-d$_6$) δ 8.25 (m, 1H), 7.88 (m, 2H), 6.97 (m, 2H), 4.71 (m, 1H), 4.45 (m, 1H), 4.21 (m, 1H), 3.80 (s, 3H), 2.96 (m, 1H), 2.74 (m, 2H), 2.13 (m, 1H), 2.10 (m, 3H), 1.8-1.5 (bm, 6H), 1.3-0.9 (bm, 7H), 0.89 (m, 6H).

ES-MS, m/z 416.4 (M+1)$^+$.

$[α]_D^{20}$=−41.12 (c=0.01 MeOH).

EXAMPLE 6

1-(4-Methoxybenzoyl-D-valinyl)-4-(1-methylpiperidin-4-yl)-piperidine Hydrochloride To a solution of 1-(4-methoxybenzoyl-D-valinyl)-4-(1-methylpiperidin-4-yl)piperidine (14.75 g, 35.5 mmol) in anhydrous CH$_2$Cl$_2$ (400 mL) cooled to 0° C. is added HCl in Et$_2$O (1 M, 35.9 mL, 35.9 mmol). After approximately 5 min, the solvent is removed in vacuo to give 16.9 g (quantitative) of the title compound as a white foam.

$^1$H NMR (DMSO-d$_6$) δ 10.0 (bs, 1H), 8.27 (m, 1H), 7.88 (m, 2H), 6.98 (m, 2H), 4.71 (m, 1H), 4.46 (m, 1H), 4.23 (m, 1H), 3.81 (s, 3H), 3.43 (s, 3H), 3.37 (m, 2H), 3.00 (m, 1H), 2.83 (m, 2H), 2.68 (m, 2H), 2.15 (bm, 1H), 1.9-1.6 (m, 4H), 1.5-1.2 (bm, 4H), 1.07 (m, 1H), 0.91 (m, 3H), 0.87 (m, 3H).

ES-MS, m/z 416.4 (M+1)$^+$.

$[α]_D^{20}$=−42.72 (c=0.01 MeOH).

Analysis for C$_{24}$H$_{37}$N$_3$O$_3$.1.0 HCl.1.2H$_2$O.0.25CH$_2$Cl$_2$: Calcd: C, 59.93; H, 8.48; N, 8.65; Cl, 9.12. Found: C, 59.67; H, 8.38; N, 8.52; Cl, 9.35.

EXAMPLE 7

1-(4-Methoxybenzoyl-D-valinyl)-4-(1-methylpiperidin-4-yl)-piperidine Methanesulfonic Acid Salt The mesylate salt is prepared by dissolving the free base in EtOAc (example concentration, 416 mg/10 mL). Separately, methanesulfonic acid is dissolved in EtOAc (example concentration, 96 mg/2 mL). The methanesulfonic acid solution is added to the base solution and the initial mixture becomes hazy. The vial is seeded, and the seeds stick to sides as the material starts to oil. The oil is allowed to sit overnight and is crystalline in the morning. The crystals are washed with a small amount of EtOAc and air dried. The yield is 460 mg (about 90%) based on a monomesylate salt, as later confirmed. The material so obtained is crystalline by photomicroscopy revealing birefringence. Analysis by DSC (differential scanning calorimetry) and TGA (thermal gravimetric analysis) indicated that the monomesylate salt had a melting point with its endotherm peak at 185° C., with 0.9% volatiles lost at 25-150° C. and 1.9% volatiles released at 150-185° C.

On larger scale, the following procedure is convenient: To a well stirred solution of the free base (125 g) in ethyl acetate (2.5 L) is added a solution of methanesulfonic acid in ethyl acetate (0.5 L) dropwise. After addition, the mixture is stirred 4 h at room temperature before the crystalline product is filtered, washed with ethyl acetate (0.5 L), and dried under vacuum (35° C., 24 h) to provide the title salt as a white crystalline solid (139.5 g, 90.0%).

melting point 182-183° C.

$[α]_D^{20}$=−43.0 (c=0.416H$_2$O).

enatiomeric excess greater than 99% by chiral HPLC

EXAMPLE 8

1-(Indole-6-carbonyl-D-valinyl)-4-(1-methylpiperidin-4-yl)-piperidine

6-Carboxyindole (4.0 g, 24.8 mmol) and 1-(D-valinyl)-4-(1-methylpiperidin-4-yl)piperidine (10.1 g, 27.8 mmol) are slurried in anhydrous CH$_2$Cl$_2$ (250 mL) and cooled to −15° C. To this slurry is added diethyl cyanophosphonate (4.5 mL, 29.8 mmol), followed by TEA (11.1 mL, 79.4 mmol) maintaining the temperature below −10° C. The reaction is allowed to warm to room temperature overnight. The following morning, if TLC indicates starting material still present, additional 6-carboxyindole (0.5 g, 3.1 mmol) and diethyl cyanophosphonate (0.5 mL, 3.3 mmol) are added, followed by TEA (1.0 mL, 7.2 mmol). After stirring for an additional 2 h, the reaction is quenched with the addition of brine (100 mL), forming an insoluble brown oil on the sides of the flask. The layers are separated and the aqueous layer is extracted with CH$_2$Cl$_2$ (3×100 mL). The organic layers are combined, dried over Na$_2$SO$_4$, filtered and concentrated. The crude material is then purified using chromatography over silica gel, with 5% (2 M NH$_3$ in MeOH)/CHCl$_3$ as the eluent, to give 9.7 g (92%) of the title compound as a light yellow foam.

$^1$H NMR (DMSO-d$_6$) δ 11.35 (s, 1H), 8.22 (m, 1H), 7.97 (s, 1H), 7.55 (s, 2H), 7.49 (s, 1H), 6.48 (s, 1H), 4.76 (m, 1H), 4.46 (m, 1H), 4.23 (m, 1H), 2.99 (m, 1H), 2.73 (m, 2H), 2.16 (m, 1H), 2.09 (m, 3H), 1.8-1.5 (m, 6H), 1.4-1.0 (m, 6H), 0.91 (m, 6H).

ES-MS, m/z 425.1 (M+1)$^+$.

Examination by photomicroscopy showed the free base to be obtained as a birefringent crystalline solid which was shown by analysis by DSC (differential scanning calorimetry) and TGA (thermal gravimetric analysis) to have a melting point with its endotherm peak at 196° C., and only about 0.4% volatiles.

EXAMPLE 9

1-(Indole-6-carbonyl-D-valinyl)-4-(1-methylpiperidin-4-yl)piperidine Hydrochloride 1-(Indole-6-carbonyl-D-valinyl)-4-(1-methylpiperidin-4-yl)piperidine (3.4 g, 8.03 mmol) is suspended in 0.2 N aqueous HCl (40.2 mL, 8.03 mmol) and sonicated. The resulting solution is lyophilized to give 3.64 g (98%) of the title compound.

$^1$H NMR

ES-MS, m/z 425.3 (M+1)$^+$.

Analysis for C$_{25}$H$_{36}$N$_4$O$_3$.1.1HCl.1.0H$_2$O: Calcd: C, 62.20; H, 8.16; N, 11.61; Cl, 8.08. Found: C, 61.91; H, 7.80; N, 11.51; Cl, 7.79.

HPLC Analysis (Method 1): 99% t$_r$=20.80 min.

EXAMPLE 10

1-(3-Methylindole-6-carbonyl-D-valinyl)-4-(1-methylpiperidin-4-yl)piperidine Hydrochloride Prepared from 1-D-valinyl-4-(1-methylpiperidin-4-yl)-piperidine hydrochloride and 3-methylindole-6-carboxylic acid using methods substantially equivalent to General Coupling Method 2. The HCl salt is prepared following General Salt Formation Method 2.

$^1$H NMR.

ES-MS, m/z 439.0 (M+1)$^+$.

Analysis for $C_{26}H_{38}N_4O_2.1.2HCl.0.9H_2O$: Calcd: C, 62.63; H, 8.29; N, 11.24; Cl, 8.53. Found: C, 62.46; H, 8.34; N, 11.03; Cl, 8.96.

Analytical HPLC (Method 1): 100%, $t_r$=25.3 min.

EXAMPLE 11

1-(3-Chloroindole-6-carbonyl-D-valinyl)-4-(1-methylpiperidin-4-yl)piperidine Hydrochloride Prepared from 1-D-valinyl-4-(1-methylpiperidin-4-yl)-piperidine hydrochloride and 3-chloroindole-6-carboxylic acid using methods substantially equivalent to General Coupling Method 1. The HCl salt is prepared following General Salt Formation Method 2.

$^1$H NMR.

ES-MS, m/z 459.0 (M+1)$^+$.

Analysis for $C_{25}H_{35}N_4O_2.1.1HCl.0.7H_2O$: Calcd: C, 58.68; H, 7.39; N, 10.95; Cl, 14.55. Found: C, 58.55; H, 7.41; N, 10.43; Cl, 14.46.

Analytical HPLC (Method 1): 100%, $t_r$=27.8 min.

EXAMPLE 12

1-(5-Chloroindole-2-carbonyl-D-valinyl)-4-(1-methylpiperidin-4-yl)piperidine Hydrochloride Prepared from 1-D-valinyl-4-(1-methylpiperidin-4-yl)-piperidine hydrochloride and 5-chloroindole-2-carboxylic acid using methods substantially equivalent to General Coupling Method 2. Purified and converted to the hydrochloride salt from by preparative reverse phase HPLC (YMC ODSA C18 5μ column, 5-95% $CH_3CN$ in $H_2O$ with 0.01% HCl) to give the HCl salt.

$^1$H NMR.

ES-MS, m/z 459.1 (M+1)$^+$.

Analysis for $C_{25}ClH_{35}N_4O_2.0.8HCl.2.2H_2O$: Calcd: C, 56.89; H, 7.68; N, 10.62; Cl, 12.09. Found: C, 56.98; H, 6.94; N, 10.45; Cl, 12.13.

Analytical HPLC (Method 1): 100%, $t_r$=25.3 min.

EXAMPLE 13

1-(Indole-6-carbonyl-D-leucinyl)-4-(1-methylpiperidin-4-yl)piperidine Hydrochloride Prepared from 1-D-leucinyl-4-(1-methylpiperidin-4-yl)-piperidine and indole-6-carboxylic acid using methods substantially equivalent to those described in General Coupling Method 1. The salt is prepared using General Salt Formation Method 2.

$^1$H NMR.

FD-MS, m/z 438.3 M$^+$.

Analysis for $C_{26}H_{38}N_4O_2.1.1HCl.1.4H_2O$: Calcd: C, 61.97; H, 8.38; N, 11.12; Cl, 7.74. Found: C, 62.00; H, 8.00; N, 11.18; Cl, 7.58.

Analytical HPLC (Method 1): >95%, $t_r$=24.43 min.

EXAMPLE 14

1-[Indole-6-carbonyl-D-(t-butyl)glycinyl]-4-(1-methylpiperidin-4-yl)piperidine Hydrochloride Prepared from 1-[D-(t-butyl)glycinyl]-4-(1-methyl-piperidin-4-yl)piperidine and indole-6-carboxylic acid using methods substantially equivalent to those described in General Coupling Method 1. The HCl salt is prepared following General Salt Formation Method 2.

$^1$H NMR.

ES-MS, m/z 439.1 (M+1)$^+$.

Analysis for $C_{26}H_{38}N_4O_2.1.1HCl.1.7H_2O$: Calcd: C, 61.31; H, 8.41; N, 11.00. Found: C, 61.43; H, 8.28; N, 10.65.

Analytical HPLC (Method 1): 100%, $t_r$=23.86 min.

EXAMPLE 15

1-(Indole-6-carbonyl-D-valinyl)-4-(1-methylpiperidin-4-yl)-piperazine

Prepared from 1-D-valinyl-4-(1-methylpiperidin-4-yl)-piperazine and indole-6-carboxylic acid using methods substantially equivalent to those described in General Coupling Method 1. The HCl salt is prepared following General Salt Formation Method 2.

$^1$H NMR.

ES-MS, m/z 426.2 (M+1)$^+$.

Analysis for $C_{24}H_{35}N_5O_2.1.4HCl.2.1H_2O$: Calcd: C, 56.03; H, 7.95; N, 13.61. Found: C, 56.05; H, 7.57; N, 13.24.

Analytical HPLC (Method 1): 100%, $t_r$=16.55 min.

EXAMPLE 16

1-(3-Chloroindole-6-carbonyl-D-valinyl)-4-(1-methylpiperidin-4-yl)piperazine Hydrochloride Prepared from 1-D-valinyl-4-(1-methylpiperidin-4-yl)-piperazine hydrochloride and 3-chloroindole-6-carboxylic acid using methods substantially equivalent to General Coupling Method 1. The HCl salt is prepared following General Salt Formation Method 1.

$^1$H NMR.

ES-MS, m/z 460.2 (M+1)$^+$.

Analysis for $C_{24}H_{34}N_5O_2Cl.2HCl.1.1H_2O$: Calcd: C, 56.05; H, 7.20; N, 13.38; Cl, 14.90. Found: C, 56.05; H, 7.08; N, 13.35; Cl, 14.82.

Analytical HPLC (Method 3): 97%, $t_r$=19.3 min.

EXAMPLE 17

1-(3-Methylindole-6-carbonyl-D-valinyl)-4-(1-methylpiperidin-4-yl)piperazine Hydrochloride Prepared from 1-D-valinyl-4-(1-methylpiperidin-4-yl)-piperazine and 3-methylindole-6-carboxylic acid using methods substantially equivalent to General Coupling Method 1. The product was purified and converted to the hydrochloride salt by preparative reverse phase HPLC (C18, 90:10 to 50:50-0.1 N HCl:$CH_3CN$).

$^1$H NMR.

ES-MS, m/z 440.3 (M+1)$^+$.

Analytical HPLC (Method 1): 100%, $t_r$=21.5 min.

EXAMPLE 18

1-(5-Chloroindole-2-carbonyl-D-valinyl)-4-(1-methylpiperidin-4-yl)piperazine Hydrochloride To a solution of D-valinyl-4-(1-methylpiperidin-4-yl)-piperazine hydrochloride (3.5 g, 8.93 mmol) and triethylamine (4.4 mL, 31.3 mmol) in dichloromethane (90 mL) is added HOBt (1.33 g, 9.82 mmol) followed by EDCI (1.9 g, 9.82 mmol). After stirring overnight the mixture is concentrated in vacuo. The residue is then chromatographed over silica gel, eluting with a gradient of 0-15% (2 N ammonia/methanol) in chloroform. The product containing fractions are combined and concentrated in vacuo to give 3.97 g (97%) of the free base of the title compound.

The free base (2.183 g, 4.75 mmol) is dissolved in 0.2 N HCl (23.8 mL) and lyophilized to give the title compound.
$^1$H NMR.
ES-MS, m/z 460.2 (M+1)$^+$.
Analysis for $C_{24}H_{34}N_5O_2Cl \cdot 2HCl \cdot 1.6H_2O$: Calcd: C, 54.12; H, 7.27; N, 13.15; Cl, 14.65. Found: C, 54.02; H, 7.13; N, 13.04; Cl, 14.65.
Analytical HPLC (Method 3): 97.7%, $t_r$=22.9 min.

EXAMPLE 19

1-(Indole-2-carbonyl-D-valinyl)-4-(1-methylpiperidin-4-yl)-piperazine Hydrochloride Prepared from 1-D-valinyl-4-(1-methylpiperidin-4-yl)-piperazine hydrochloride and indole-2-carboxylic acid using methods substantially equivalent to General Coupling Method 1. The HCl salt is prepared following General Salt Formation Method 1.
$^1$H NMR.
ES-MS, m/z 426.3 (M+1)$^+$.
Analysis for $C_{24}H_{35}N_5O_2 \cdot 2HCl \cdot 1.6H_2O$: Calcd: C, 57.45; H, 8.06; N, 13.96; Cl, 7.77. Found: C, 57.37; H, 7.39; N, 13.68; Cl, 8.15.

EXAMPLE 20

1-[Indole-6-carbonyl-D-(t-butyl)glycinyl]-4-(1-methylpiperidin-4-yl)piperazine Hydrochloride Prepared from 1-D-(t-butyl)glycinyl-4-(1-methylpiperidin-4-yl)piperazine and indole-6-carboxylic acid using methods substantially equivalent to those described in General Coupling Method 1. The HCl salt is prepared following General Salt Formation Method 2.
$^1$H NMR.
ES-MS, m/z 440.3 (M+1)$^+$.
Analysis for $C_{25}H_{37}N_5O \cdot 2.1HCl \cdot 1.9H_2O$: Calcd: C, 54.55; H, 7.86; N, 12.72; Cl, 13.53. Found: C, 54.39; H, 7.72; N, 12.34; Cl, 13.85.
Analytical HPLC (Method 1): 94%, $t_r$=17.07 min.

EXAMPLE 21

1-(Indole-6-carbonyl-D-isoleucinyl)-4-(1-methylpiperidin-4-yl)-piperazine Hydrochloride Prepared from 1-D-isoleucinyl-4-(1-methylpiperidin-4-yl)-piperazine and indole-6-carboxylic acid using methods substantially equivalent to those described in General Coupling Method 1. The HCl salt is prepared following General Salt Formation Method 2.
$^1$H NMR.
ES-MS, m/z 440.3 (M+1)$^+$.
Analysis for $C_{25}H_{37}N_5O \cdot 2.3HCl \cdot 1.8H_2O$: Calcd: C, 54.19; H, 7.77; N, 12.64; Cl, 14.72. Found: C, 53.91; H, 7.37; N, 12.02; Cl, 14.90.
Analytical HPLC (Method 1): 95%, $t_r$=18.08 min.

EXAMPLE 22

1-(Indole-6-carbonyl-D-leucinyl)-4-(1-methylpiperidin-4-yl)-piperazine Hydrochloride Prepared from 1-D-leucinyl-4-(1-methylpiperidin-4-yl)-piperazine and indole-6-carboxylic acid using methods substantially equivalent to those described in General Coupling Method 1. The HCl salt is prepared following General Salt Formation Method 2.
$^1$H NMR.
ES-MS, m/z 440.2 (M+1)$^+$.
Analysis for $C_{25}H_{37}N_5O \cdot 1.1HCl \cdot 3.0H_2O$: Calcd: C, 56.25; H, 8.33; N, 13.12; Cl, 7.31. Found: C, 56.34; H, 7.64; N, 12.75; Cl, 7.06.
Analytical HPLC (Method 1): 100%, $t_r$=18.72 min Further information for following examples:

HPLC Analysis (Method A): Waters Symmetry, C18 (4.6×250 mm) column. The elution system consisted of linear gradient from 95:5 (0.1% TFA in $H_2O$)/(0.1% TFA in $CH_3CN$) to 5:95 (0.1% TFA in $H_2O$)/(0.1% TFA in $CH_3CN$) over 20 min, followed by 5:95 (0.1% TFA in $H_2O$)/(0.1% TFA in $CH_3CN$) isocratic over 10 min. The flow rate was 1 mL/min. UV Detection was performed at 254 nm unless otherwise noted.

API-MS (atmospheric pressure chemical ionization mass spectra) were obtained on a PESciex API 150EX with a heated nebulizer and nitrogen as the reagent gas in positive ion mode.

CI-MS (Chemical ionization mass spectra) were obtained on a Shimadzu 5000 direct insertion mass spectrometer in chemical ionization mode utilizing methane as the reagent gas.

The following further abbreviations are used: CMA (chloroform:methanol:concentrated ammonium hydroxide 80:18:2), DEPC (diethyl cyanophosphonate).

General Coupling Method 4: The amine or amine hydrochloride salt (1 eq) and triethylamine (1-3 eq) are dissolved in dichloromethane (0.1-0.5 M) and an acid chloride (about 1.1 eq) is added. After stirring overnight, the reaction mixture is quenched with saturated $NaHCO_3$ solution. The aqueous layer is extracted twice with dichloromethane, and the combined organic layers are dried over $Na_2SO_4$, filtered and concentrated in vacuo. If necessary, the product is purified by chromatography over silica gel, eluting with a gradient of 0-10% 2 N ammonia/methanol in dichloromethane. The product-containing fractions are then combined and concentrated in vacuo. Alternatively, the crude product is purified by reverse phase HPLC on C-18 using a 5 to 95% gradient of acetonitrile in $H_2O$ with 0.01% HCl over 12 min. Freeze-drying gives the product as its HCl salt.

EXAMPLE 23

1-(3-Chloroindole-6-carbonyl-D-ethylglycinyl)-4-(1-methyl-piperidin-4-yl)piperidine Hydrochloride Prepared from 1-D-ethylglycinyl-4-(1-methylpiperidin-4-yl)piperidine dihydrochloride and 3-chloroindole-6-carboxylic acid using methods substantially equivalent to General Coupling Method 1. The HCl salt is prepared following General Salt Formation Method 1.
$^1$H NMR.
ES-MS, m/z 445.2 (M+1)$^+$.
Analysis for $C_{24}H_{33}N_4O_2Cl \cdot 1.0HCl \cdot 1.6H_2O$: Calcd: C, 56.49; H, 7.35; N, 10.98; Cl, 13.90. Found: C, 56.58; H, 6.95; N, 10.93; Cl, 13.44.
Analytical HPLC (Method 2): >97%, $t_r$=20.7 min.

EXAMPLE 24

1-(5-Chloroindole-2-carbonyl-D-ethylglycinyl)-4-(1-methyl-piperidin-4-yl)piperidine Hydrochloride Prepared from 1-D-ethylglycinyl-4-(1-methylpiperidin-4-yl)piperidine dihydrochloride and 5-chloroindole-2-carboxylic acid using methods substantially equivalent to General Coupling Method 1. The HCl salt is prepared following General Salt Formation Method 1.
$^1$H NMR.
ES-MS, m/z 445.2 (M+1)$^+$.
Analysis Calcd. For $C_{24}H_{33}N_4O_2Cl \cdot 1.0HCl \cdot 2.1H_2O$: Calcd: C, 55.51; H, 7.41; N, 10.79; Cl, 13.66. Found: C, 55.61; H, 6.90; N, 10.77; Cl, 13.57.
Analytical HPLC (Method 2): >90%, $t_r$=22.3 min.

EXAMPLE 25

1-(4-Methoxybenzoyl-D-ethylglycinyl)-4-(1-methylpiperidin-4-yl)piperidine Hydrochloride Prepared from 1-D-ethylglycinyl-4-(1-methylpiperidin-4-yl)piperidine dihydrochloride and 4-methoxybenzoyl chloride using methods substantially equivalent to General Coupling Method 4. Purification by the reverse phase chromatography option gives the HCl salt.
$^1$H NMR.
ES-MS, m/z 402.3 (M+1)$^+$.
Analysis for $C_{23}H_{35}N_3O_3 \cdot 1.0HCl \cdot 1.4H_2O$: Calcd: C, 59.63; H, 8.44; N, 9.07. Found: C, 59.75; H, 8.24; N, 8.91.

EXAMPLE 26

1-[(3-Fluoro-4-methoxybenzoyl)-D-ethylglycinyl)]-4-(1-methylpiperidin-4-yl)piperidine Hydrochloride Prepared from l-D-ethylglycinyl-4-(1-methylpiperidin-4-yl)piperidine dihydrochloride and 3-fluoro-4-methoxybenzoic acid using methods substantially equivalent to General Coupling Method 1 with reverse phase purification as described in General Coupling Method 4 to give the HCl salt.
$^1$H NMR.
ES-MS, m/z 420.3 (M+1)$^+$.
Analysis for $C_{23}H_{34}N_3O_3F \cdot 1.7HCl \cdot 1.0H_2O$: Calcd: C, 55.30; H, 7.61; N, 8.41. Found: C, 55.22; H, 7.22; N, 8.42.

EXAMPLE 27

1-(6-Chlorobenzo[b]thiophene-2-carbonyl-D-ethylglycinyl)-4-(1-methylpiperidin-4-yl)piperidine Hydrochloride Prepared from 1-D-ethylglycinyl-4-(1-methylpiperidin-4-yl)piperidine dihydrochloride and 6-chlorobenzo[b]thiophene-2-carboxylic acid using methods substantially equivalent to General Coupling Method 1 with reverse phase purification as described in General Coupling Method 4 to give the HCl salt.
$^1$H NMR.
ES-MS, m/z 462.2 (M+1)$^+$.
Analysis for $C_{24}H_{32}N_3O_2SCl \cdot 1.0HCl \cdot 1.2H_2O$: Calcd: C, 55.42; H, 6.86; N, 8.08. Found: C, 55.50; H, 6.65; N, 8.04.

EXAMPLE 28

1-[3-Chloroindole-6-carbonyl-D-propylglycinyl]-4-(1-methylpiperidin-4-yl)piperidine Hydrochloride Prepared from 1-D-propylglycinyl-4-(1-methylpiperidin-4-yl)piperidine dihydrochloride and 3-chloroindole-6-carboxylic acid using methods substantially equivalent to General Coupling Method 1. The HCl salt is prepared following General Salt Formation Method 1.
$^1$H NMR.
ES-MS, m/z 459.3 (M+1)$^+$.
Analysis for $C_{25}H_{35}N_4O_2Cl \cdot 1.0HCl \cdot 2.3H_2O$: Calcd: C, 55.92; H, 7.62; N, 10.44; Cl, 13.21. Found: C, 55.84; H, 6.95; N, 10.35; Cl, 13.16.
Analytical HPLC (Method 2): >90%, $t_r$=22.3 min.

EXAMPLE 29

1-[5-Chloroindole-2-carbonyl-D-propylglycinyl]-4-(1-methylpiperidin-4-yl)piperidine Hydrochloride Prepared from 1-D-propylglycinyl-4-(1-methylpiperidin-4-yl)piperidine dihydrochloride and 5-chloroindole-2-carboxylic acid using methods substantially equivalent to General Coupling Method 1. The HCl salt is prepared following General Salt Formation Method 1.
$^1$H NMR.
ES-MS, m/z 459.3 (M+1)$^+$.
Analysis for $C_{25}H_{35}N_4O_2Cl \cdot 0.9HCl \cdot 1.9H_2O$: Calcd: C, 57.08; H, 7.61; N, 10.65; Cl, 12.81. Found: C, 57.09; H, 6.98; N, 10.71; Cl, 12.74.
Analytical HPLC (Method 2): >91%, $t_r$=24.0 min.

EXAMPLE 30

1-[4-Methoxybenzoyl-D-propylglycinyl]-4-(1-methylpiperidin-4-yl)piperidine Hydrochloride Prepared from 1-D-propylglycinyl-4-(1-methylpiperidin-4-yl)piperidine dihydrochloride and 4-methoxybenzoyl chloride using methods substantially equivalent to General Coupling Method 4. Purification by the reverse phase chromatography option gives the HCl salt.
$^1$H NMR.
ES-MS, m/z 416.3 (M+1)$^+$.
Analysis for $C_{24}H_{37}N_3O_3 \cdot 1.0HCl \cdot 1.4H_2O$: Calcd: C, 60.40; H, 8.62; N, 8.81. Found: C, 60.49; H, 8.38; N, 8.78.

EXAMPLE 31

1-[(3-Fluoro-4-methoxybenzoyl)-D-propylglycinyl]-4-(1-methylpiperidin-4-yl)piperidine Hydrochloride Prepared from 1-D-propylglycinyl-4-(1-methylpiperidin-4-yl)piperidine dihydrochloride and 3-fluoro-4-methoxybenzoic acid using methods substantially equivalent to General Coupling Method 1 with reverse phase purification as described in General Coupling Method 4 to give the HCl salt.

¹H NMR.
ES-MS, m/z 434.3 (M+1)⁺.
Analysis for $C_{24}H_{36}N_3O_3F \cdot 1.1HCl \cdot 1.6H_2O$: Calcd: C, 57.36; H, 8.08; N, 8.36. Found: C, 57.36; H, 7.80; N, 8.33.

EXAMPLE 32

1-[6-Chlorobenzo[b]thiophene-2-carbonyl-D-propylglycinyl]-4-(1-methylpiperidin-4-yl)piperidine Hydrochloride Prepared from 1-D-propylglycinyl-4-(1-methylpiperidin-4-yl)piperidine dihydrochloride and 6-chlorobenzo[b]thiophene-2-carboxylic acid using methods substantially equivalent to General Coupling Method 1. The HCl salt is prepared following General Salt Formation Method 1 with reverse phase purification as described in General Coupling Method 4 to give the HCl salt.

¹H NMR.
ES-MS, m/z 476.2 (M+1)⁺.
Analysis for $C_{25}H_{34}N_3O_2SCl \cdot 1.0HCl \cdot 1.3H_2O$: Calcd: C, 56.02; H, 7.07; N, 7.84. Found: C, 55.95; H, 6.79; N, 7.74.

EXAMPLE 33

1-[3-Chloroindole-6-carbonyl-D-butylglycinyl]-4-(1-methylpiperidin-4-yl)piperidine Hydrochloride Prepared from 1-D-butylglycinyl-4-(1-methylpiperidin-4-yl)piperidine dihydrochloride and 3-chloroindole-6-carboxylic acid using methods substantially equivalent to General Coupling Method 1. The HCl salt is prepared following General Salt Formation Method 1.

¹H NMR.
ES-MS, m/z 473.3 (M+1)⁺.
Analysis for $C_{26}H_{37}N_4O_2Cl \cdot 0.9HCl \cdot 2.0H_2O$: Calcd: C, 57.63; H, 7.79; N, 10.34; Cl, 12.43. Found: C, 57.48; H, 7.49; N, 10.41; Cl, 12.36.
Analytical HPLC (Method 2): >96%, $t_r$=23.9 min.

EXAMPLE 34

1-[5-Chloroindole-2-carbonyl-D-butylglycinyl]-4-(1-methylpiperidin-4-yl)piperidine Hydrochloride Prepared from 1-D-butylglycinyl-4-(1-methylpiperidin-4-yl)piperidine dihydrochloride and 5-chloroindole-2-carboxylic acid using methods substantially equivalent to General Coupling Method 1. The HCl salt is prepared following General Salt Formation Method 1.

¹H NMR.
ES-MS, m/z 473.3 (M+1)⁺.
Analysis Calcd. For $C_{26}H_{37}N_4O_2Cl \cdot 0.9HCl \cdot 1.9H_2O$: Calcd: C, 57.82; H, 7.78; N, 10.37; Cl, 12.47. Found: C, 57.93; H, 7.24; N, 10.54; Cl, 12.20.
Analytical HPLC (Method 2): >95%, $t_r$=25.5 min.

Preparation of Intermediates

1-N-Boc-D-ethylglycinyl-4-(1-methylpiperidin-4-yl)piperazine

Prepared from Boc-D-ethylglycine and 4-(1-methylpiperidin-4-yl)piperazine using methods substantially equivalent to General Coupling Method 1.
¹H NMR.
ES-MS, m/z 369.3 (M+1)⁺.
Analysis for $C_{19}H_{36}N_4O_3 \cdot 0.3H_2O$: Calcd: C, 61.03; H, 9.87; N, 14.98. Found: C, 61.02; H, 9.39; N, 14.87.

1-N-Boc-D-propylglycinyl-4-(1-methylpiperidin-4-yl)piperazine

Prepared from Boc-D-propylglycine and 4-(1-methyl-piperidin-4-yl)piperazine using methods substantially equivalent to General Coupling Method 1.
¹H NMR.
ES-MS, m/z 383.3 (M+1)⁺.

1-N-Boc-D-butylglycinyl-4-(1-methylpiperidin-4-yl)piperazine

Prepared from Boc-D-butylglycine and 4-(1-methylpiperidin-4-yl)piperazine using methods substantially equivalent to General Coupling Method 1.
¹H NMR.
ES-MS, m/z 397.3 (M+1)⁺.
Analysis for $C_{21}H_{40}N_4O_3 \cdot 0.3H_2O$: Calcd: C, 62.75; H, 10.18; N, 13.94. Found: C, 62.89; H, 9.71; N, 13.88.

N-Boc-D-Propargylglycine.

Method A-1: A solution of di-tert-butyl dicarbonate (5.7 g, 26.4 mmol) in 1,4-dioxane (20 mL) is added into an efficiently stirred solution of D-propargylglycine (2.5 g, 22.1 mmol) and NaOH (1.86 g, 46.5 mmol) in water (45 mL) at 0° C. The mixture is stirred 30 min at 0° C. and 3.5 h at room temperature. The mixture is concentrated to one half volume at 35° C. under vacuum. The solution is cooled in an ice/water bath and acidified to pH 2-3 with potassium hydrogen sulfate solution (2 N). The mixture is extracted with ethyl acetate; and the organic layer is washed with water, dried over anhydrous sodium sulfate, and concentrated under vacuum to provide the titled compound (4.6 g, 97%).
¹H NMR (CDCl₃).
APCI-MS, m/e=214 (M+1).

1-(N-Boc-D-Propargylglycinyl)-4-(1-methylpiperidin-4-yl)-piperazine

Method B-1: To a mixture of N-Boc-D-propargylglycine (4.6 g, 21.6 mmol), 4-(1-methylpiperidin-4-yl)piperazine (3.91 g, 21.6 mmol), HOBt (2.88 g, 21.6 mmol), EDCI (5.3 g, 28 mmol), CH₂Cl₂ (250 mL) is added diisopropylethylamine (7.9 mL, 43.2 mmol) at room temperature. The mixture is stirred overnight. The mixture is diluted with dichloromethane and water. The layers are separated; and the organic layer is dried over anhydrous sodium sulfate, filtered, and concentrated under vacuum. The residue is purified by chromatography on silica gel with hexanes/CMA to provide the titled compound (3.4 g, 41%).
¹H NMR (CDCl₃).
APCI-MS, m/e=379 (M+1).

N-Boc-D-Allylglycine

Using methods substantially equivalent to that described in Method A-1, the titled compound is prepared from D-allylglycine and di-tert-butyl dicarbonate (81%).
$^1$H NMR (CDCl$_3$).
APCI-MS, m/e=216 (M+1).

1-(N-Boc-D-Allylglycinyl)-4-(1-methylpiperidin-4-yl)piperazine

Using methods substantially equivalent to that described in Method B-1, the titled compound is prepared from N-Boc-D-allylglycine and 4-(1-methylpiperidin-4-yl)piperazine (31%).
$^1$H NMR (CDCl$_3$).
APCI-MS, m/e=380 (M+1).

1-D-Ethylglycinyl-4-(1-methylpiperidin-4-yl)piperazine Trihydrochloride

Prepared from 1-Boc-D-ethylglycinyl-4-(1-methylpiperidin-4-yl)piperazine using methods substantially equivalent to those described in General Deprotection Method 2.
$^1$H NMR.
ES-MS, m/z 269.2 (M+1)$^+$.
Analysis for C$_{14}$H$_{28}$N$_4$O·3HCl: Calcd: C, 44.51; H, 8.27; N, 14.83; Cl, 28.15. Found: C, 44.48; H, 8.02; N, 14.79; Cl, 27.77.

1-D-Propylglycinyl-4-(1-methylpiperidin-4-yl)piperazine Trihydrochloride

Prepared from 1-Boc-D-propylglycinyl-4-(1-methylpiperidin-4-yl)piperazine using methods substantially equivalent to those described in General Deprotection Method 2.
$^1$H NMR.
ES-MS, m/z 283.3 (M+1)$^+$.
Analysis for C$_{15}$H$_{30}$N$_4$O·3HCl·0.2H$_2$O: Calcd: C, 45.68; H, 8.28; N, 14.21; Cl, 26.97. Found: C, 45.86; H, 8.29; N, 14.11; Cl, 26.85.

1-D-Butylglycinyl-4-(1-methylpiperidin-4-yl)piperazine Trihydrochloride

Prepared from 1-Boc-D-butylglycinyl-4-(1-methylpiperidin-4-yl)piperazine using methods substantially equivalent to those described in General Deprotection Method 2.
$^1$H NMR.
ES-MS, m/z 297.3 (M+1)$^+$.
Analysis for C$_{16}$H$_{32}$N$_4$O·2.9HCl·1.2H$_2$O: Calcd: C, 45.45; H, 8.65; N, 13.25; Cl, 24.32. Found: C, 45.23; H, 8.27; N, 13.00; Cl, 24.39.

1-(D-Propargylglycinyl)-4-(1-methylpiperidin-4-yl)piperazine

Method C-1: A mixture of 1-(1-Boc-D-propargylglycinyl)-4-(1-methylpiperidin-4-yl)piperazine (3.4 g, 9 mmol), methanol (50 mL), and anisole (15 mL) is cooled to 0° C. Concentrated HCl (20 mL) is added dropwise. The mixture is stirred 2 h at room temperature. The mixture is concentrated under vacuum. The residue is dissolved in methanol and applied to SCX resin (activated with 5% acetic acid in methanol and washed with methanol), washed with methanol, and eluted with saturated ammonia in methanol. The product fraction is concentrated under vacuum to provide the titled compound as an oil (2.1 g, 84%).
$^1$H NMR (CDCl$_3$).
APCI-MS, m/e=279 (M+1).

1-(D-Allylglycinyl)-4-(1-methylpiperidin-4-yl)piperazine

Method C-2: To a stirred solution of 1-(Boc-D-allylglycinyl)-4-(1-methylpiperidin-4-yl)piperazine (2.2 g) in dichloromethane (40 mL) at 0° C. is added trifluoroacetic acid (20 mL). The solution is allowed to warm to room temperature over 3 h. The solvents are removed under vacuum. The residue is dissolved in methanol and applied to a SCX column (pre-washed with 5% acetic acid in methanol and methanol), washed with methanol and eluted with saturated ammonia in methanol. The product fraction is collected and concentrated under vacuum to provide the titled compound (1.6 g, quantitative) as a yellow oil.
$^1$H NMR (CD$_3$OD).
APCI-MS, m/e 281 (C$_{15}$H$_{28}$N$_4$O+1).

EXAMPLE 35

1-(Indole-6-carbonyl-D-ethylglycinyl)-4-(1-methylpiperidin-4-yl)piperazine Hydrochloride Prepared from 1-D-ethylglycinyl-4-(1-methylpiperidin-4-yl)piperazine trihydrochloride and indole-6-carboxylic acid using methods substantially equivalent to General Coupling Method 1. The HCl salt is prepared following General Salt Formation Method 1.
$^1$H NMR.
ES-MS, m/z 412.2 (M+1)$^+$.
Analysis for C$_{23}$H$_{33}$N$_5$O$_2$·1.0HCl·0.9H$_2$O: Calcd: C, 59.51; H, 7.77; N, 15.09. Found: C, 59.63; H, 7.89; N, 15.09.
Analytical HPLC (Method 2): >98%, t$_r$=11.3 min.

EXAMPLE 36

1-(5-Chloroindole-2-carbonyl-D-ethylglycinyl)-4-(1-methyl-piperidin-4-yl)piperazine Hydrochloride Prepared from l-D-ethylglycinyl-4-(1-methylpiperidin-4-yl)piperazine trihydrochloride and 5-chloroindole-2-carboxylic acid using methods substantially equivalent to General Coupling Method 1. The HCl salt is prepared following General Salt Formation Method 1.
$^1$H NMR.
ES-MS, m/z 446.2 (M+1)$^+$.
Analysis for C$_{23}$H$_{32}$N$_5$O$_2$Cl·1.0HCl·2.0H$_2$O: Calcd: C, 53.28; H, 7.19; N, 13.51; Cl, 13.68. Found: C, 53.14; H, 6.51; N, 13.29; Cl, 13.45.
Analytical HPLC (Method 2): >99%, t$_r$=18.9 min.

EXAMPLE 37

1-(4-Methoxybenzoyl-D-ethylglycinyl)-4-(1-methylpiperidin-4-yl)piperazine Hydrochloride Prepared from 1-D-ethylglycinyl-4-(1-methylpiperidin-4-yl)piperazine trihydrochloride and 4-methoxybenzoyl chloride using methods substantially equivalent to General Coupling Method 4. The HCl salt is prepared following General Salt Formation Method 1.
$^1$H NMR.
ES-MS, m/z 403.3 (M+1)$^+$.

Analysis for $C_{22}H_{34}N_4O_3 \cdot HCl \cdot 0.4H_2O$: Calcd: C, 59.35; H, 7.88; N, 12.59; Cl, 7.96. Found: C, 59.38; H, 8.21; N, 12.54; Cl, 8.05.

Analytical HPLC (Method 2): >99%, $t_r$=7.2 min.

EXAMPLE 38

1-(6-Chlorobenzo[b]thiophene-2-carbonyl-D-ethylglycinyl)-4-(1-methylpiperidin-4-yl)piperazine Hydrochloride Prepared from 1-D-ethylglycinyl-4-(1-methylpiperidin-4-yl)piperazine trihydrochloride and 6-chlorobenzo[b]thiophene-2-carboxylic acid using methods substantially equivalent to General Coupling Method 1. The HCl salt is prepared following General Salt Formation Method 1.

$^1$H NMR.

ES-MS, m/z 463.2 (M+1)$^+$.

Analysis for $C_{23}H_{31}N_4O_2SCl \cdot HCl \cdot 1.4H_2O$: Calcd: C, 52.65; H, 6.68; N, 10.68. Found: C, 52.72; H, 6.70; N, 10.34.

Analytical HPLC (Method 2): >99%, $t_r$=17.8 min.

EXAMPLE 39

1-[Indole-6-carbonyl-D-propylglycinyl]-4-(1-methylpiperidin-4-yl)piperazine Hydrochloride Prepared from 1-D-propylglycinyl-4-(1-methylpiperidin-4-yl)piperazine trihydrochloride and indole-6-carboxylic acid using methods substantially equivalent to General Coupling Method 1. The HCl salt is prepared following Salt Formation Method 1.

$^1$H NMR.

ES-MS, m/z 426.3 (M+1)$^+$.

Analysis for $C_{24}H_{35}N_5O_2 \cdot HCl \cdot 1.9H_2O$: Calcd: C, 58.20; H, 7.90; N, 14.14; Cl, 7.16. Found: C, 58.31; H, 7.75; N, 14.07; Cl, 7.14.

Analytical HPLC (Method 2): >99%, $t_r$=14.4 min.

EXAMPLE 40

1-[5-Chloroindole-2-carbonyl-D-propylglycinyl]-4-(1-methylpiperidin-4-yl)piperazine Hydrochloride Prepared from 1-D-propylglycinyl-4-(1-methylpiperidin-4-yl)piperazine trihydrochloride and 5-chloroindole-2-carboxylic acid using methods substantially equivalent to General Coupling Method 1. The HCl salt is prepared following General Salt Formation Method 1.

$^1$H NMR.

ES-MS, m/z 460.2 (M+1)$^+$.

Analysis for $C_{24}H_{34}N_5O_2Cl \cdot 0.9HCl \cdot 2.4H_2O$: Calcd: C, 53.77; H, 7.46; N, 13.06; Cl, 12.57. Found: C, 53.84; H, 6.70; N, 12.96; Cl, 12.40.

Analytical HPLC (Method 2): >99%, $t_r$=19.8 min.

EXAMPLE 41

1-[4-Methoxybenzoyl-D-propylglycinyl]-4-(1-methylpiperidin-4-yl)piperazine Hydrochloride Prepared from 1-D-propylglycinyl-4-(1-methylpiperidin-4-yl)piperazine trihydrochloride and 4-methoxybenzoyl chloride using methods substantially equivalent to General Coupling Method 4. The HCl salt is prepared following General Salt Formation Method 1.

$^1$H NMR.

ES-MS, m/z 417.3 (M+1)$^+$.

Analysis for $C_{23}H_{36}N_4O_3 \cdot HCl$: Calcd: C, 60.98; H, 8.23; N, 12.37; Cl, 7.83. Found: C, 60.99; H, 8.33; N, 12.35; Cl, 7.75.

Analytical HPLC (Method 2): >99%, $t_r$=11.6 min.

EXAMPLE 42

1-[6-Chlorobenzo[b]thiophene-2-carbonyl-D-propylglycinyl]-4-(1-methylpiperidin-4-yl)piperazine Hydrochloride Prepared from 1-D-propylglycinyl-4-(1-methylpiperidin-4-yl)piperazine trihydrochloride and 6-chlorobenzo[b]thiophene-2-carboxylic acid using methods substantially equivalent to General Coupling Method 1 with reverse phase purification as described in General Coupling Method 4 to give the dihydrochloride salt.

$^1$H NMR.

ES-MS, m/z 477.3 (M+1)$^+$.

Analysis for $C_{24}H_{33}N_4O_2SCl \cdot 3.3HCl \cdot 0.1H_2O$: Calcd: C, 48.11; H, 6.14; N, 9.35. Found: C, 47.81; H, 5.74; N, 8.96.

Analytical HPLC (Method 2): >96%, $t_r$=19.5 min.

EXAMPLE 43

1-[Indole-6-carbonyl-D-butylglycinyl]-4-(1-methylpiperidin-4-yl)piperazine Hydrochloride Prepared from 1-D-butylglycinyl-4-(1-methylpiperidin-4-yl)piperazine trihydrochloride and indole-6-carboxylic acid using methods substantially equivalent to General Coupling Method 1. The HCl salt is prepared following General Salt Formation Method 1.

$^1$H NMR.

ES-MS, m/z 440.3 (M+1)$^+$.

Analysis for $C_{25}H_{37}N_5O_2 \cdot HCl \cdot 2.3H_2O$: Calcd: C, 58.14; H, 8.12; N, 13.56; Cl, 6.86. Found: C, 58.15; H, 7.46; N, 13.41; Cl, 6.94.

Analytical HPLC (Method 2): >99%, $t_r$=16.8 min.

EXAMPLE 44

1-[5-Chloroindole-2-carbonyl-D-butylglycinyl]-4-(1-methylpiperidin-4-yl)piperazine Hydrochloride Prepared from 1-D-butylglycinyl-4-(1-methylpiperidin-4-yl)piperazine trihydrochloride and 5-chloroindole-2-carboxylic acid using methods substantially equivalent to General Coupling Method 1. The HCl salt is prepared following General Salt Formation Method 1.

$^1$H NMR.

ES-MS, m/z 474.2 (M+1)$^+$.

Analysis for $C_{25}H_{36}N_5O_2Cl \cdot HCl \cdot 1.5H_2O$: Calcd: C, 55.86; H, 7.50; N, 13.03; Cl, 13.19. Found: C, 55.95; H, 7.00; N, 12.94; Cl, 13.09.

Analytical HPLC (Method 2): >99%, $t_r$=21.6 min.

EXAMPLE 45

1-[4-Methoxybenzoyl-D-butylglycinyl]-4-(1-methylpiperidin-4-yl)piperazine Hydrochloride Prepared from 1-D-butylglycinyl-4-(1-methylpiperidin-4-yl)piperazine trihydrochloride and 4-methoxybenzoyl chloride using methods substantially equivalent to General Coupling Method 4. The HCl salt is prepared following General Salt Formation Method 1.
$^1$H NMR.
ES-MS, m/z 431.3 (M+1)$^+$.
Analysis for $C_{24}H_{38}N_4O_3 \cdot HCl \cdot 0.8H_2O$: Calcd: C, 60.00; H, 8.31; N, 11.66; Cl, 7.38. Found: C, 60.00; H, 8.35; N, 11.54; Cl, 7.30.
Analytical HPLC (Method 2): >99%, $t_r$=14.7 min.

EXAMPLE 46

1-[6-Chlorobenzo[b]thiophene-2-carbonyl-D-butylglycinyl]-4-(1-methylpiperidin-4-yl)piperazine Hydrochloride Prepared from 1-D-butylglycinyl-4-(1-methylpiperidin-4-yl)piperazine trihydrochloride and 6-chlorobenzo[b]thiophene-2-carboxylic acid using methods substantially equivalent to General Coupling Method 1. The HCl salt is prepared following General Salt Formation Method 1.
$^1$H NMR.
ES-MS, m/z 491.2 (M+1)$^+$.
Analysis for $C_{25}H_{35}N_4O_2SCl \cdot HCl \cdot 2H_2O$: Calcd: C, 53.28; H, 7.15; N, 9.94. Found: C, 52.92; H, 6.84; N, 10.23.
Analytical HPLC (Method 2): >99%, $t_r$=21.4 min.

EXAMPLE 47

1-(5-Chloroindole-2-carbonyl-D-propargylglycinyl)-4-(1-methylpiperidin-4-yl)piperazine Method D-1: To a mixture of 1-(D-propargylglycinyl)-4-(1-methylpiperidin-4-yl)piperazine (725 mg, 2.6 mmol), 5-chloroindole-2-carboxylic acid (510 mg, 2.6 mmol), HOBt (363 mg, 2.6 mmol), DMF (8 mL), and triethylamine (0.72 mL, 5.7 mmol) is added DCC (700 mg, 3.4 mmol). The mixture is stirred overnight at room temperature. The precipitate that formed is removed by filtration and washed with DMF. The filtrate is concentrated under vacuum. The residue is dissolved in methanol and applied to SCX resin (activated with 5% acetic acid and rinsed with methanol), washed with methanol and eluted with saturated ammonia/methanol solution. The product fractions are concentrated under vacuum, and the residue is purified by chromatography on silica gel (dichloromethane and CMA) to provide the titled compound (730 mg, 62%).
$^1$H NMR (CDCl$_3$).
APCI-MS, m/e=456 (M+1).

EXAMPLE 48

1-(5-Chloroindole-2-carbonyl-D-propargylglycinyl)-4-(1-methylpiperidin-4-yl)piperazine Hydrochloride Salt Formation Method 3: To a solution of 1-(5-chloroindole-2-carbonyl-D-propargylglycinyl)-4-(1-methylpiperidin-4-yl)piperazine (700 mg, 1.54 mmol) in acetonitrile (200 mL) is added hydrogen chloride (1.54 mL, 1.54 mmol, 1 N in diethyl ether) dropwise at 0° C. The solvent is evaporated under vacuum. The residue is dissolved in methanol, concentrated under vacuum, and dried in vacuum oven at 40° C. to provide the titled compound (768 mg, quantitative).
$[\alpha]^{25}_D$ –23.0° (c 0.30, Methanol)
Melting Point=174-185° C. with decomposition.
$^1$H NMR (CD$_3$OD).
APCI-MS, m/e=456 ($C_{24}H_{30}ClN_5O_2$+1).
TLC $R_f$=0.34 (3:2 CH$_2$Cl$_2$:CMA)
Analysis for $C_{24}H_{30}ClN_5O_2 \cdot 0.9HCl \cdot 0.6H_2O$: Calcd: C, 57.38; H, 6.47; N, 13.92; Cl, 13.76. Found: C, 57.47; H, 6.50; N, 13.76; Cl, 13.74.
HPLC Analysis (Method A): >99% $t_r$=12.9 min.

EXAMPLE 49

1-(Indole-6-carbonyl-D-propargylglycinyl)-4-(1-methylpiperidin-4-yl)piperazine

Using methods substantially equivalent to that described in Method D-1, the subtitled compound is prepared from 1-(D-propargylglycinyl)-4-(1-methylpiperidin-4-yl)piperazine and indole-6-carboxylic acid (76%).
$^1$H NMR (CDCl$_3$).
APCI-MS, m/e=422 (M+1).

EXAMPLE 50

1-(Indole-6-carbonyl-D-propargylglycinyl)-4-(1-methylpiperidin-4-yl)piperazine Hydrochloride Using methods substantially equivalent to those described in Salt Formation Method 3, the titled compound is prepared from 1-(indole-6-carbonyl-D-propargylglycinyl)-4-(1-methyl-piperidin-4-yl)piperazine (96%).
$[\alpha]^{25}_D$ –14.1° (c 0.29, Methanol)
Melting Point=170-180° C. with decomposition.
$^1$H NMR (CD$_3$OD).
APCI-MS, m/e=422 ($C_{24}H_{31}N_5O_2$+1).
TLC $R_f$=0.23 (3:2 CH$_2$Cl$_2$:CMA)
Analysis for $C_{24}H_{31}N_5O_2 \cdot 1.2$ HCl$\cdot 1.2H_2O$: Calcd: C, 59.20; H, 7.16; N, 14.38; Cl, 8.74. Found: C, 59.41; H, 7.01; N, 14.14; Cl, 8.93.
HPLC Analysis (Method A): >99% $t_r$=9.9 min.

EXAMPLE 51

1-(6-Chlorobenzo[b]thiophene-2-carbonyl-D-propargylglycinyl)-4-(1-methylpiperidin-4-yl)piperazine Using methods substantially equivalent to that described in Method D-1, the titled compound is prepared from 1-(D-propargylglycinyl)-4-(1-methylpiperidin-4-yl)piperazine and 6-chlorobenzo[b]thiophene-2-carboxylic acid (76%).
$^1$H NMR (CDCl$_3$).
APCI-MS, m/e=472 (M+1).

EXAMPLE 52

1-(6-Chlorobenzo[b]thiophene-2-carbonyl-D-propargylglycinyl)-4-(1-methylpiperidin-4-yl)piperazine Hydrochloride Using methods substantially equivalent to those described in Salt Formation Method 3, the subtitled compound is prepared from 1-(6-chlorobenzo[b]thiophene-2-carbonyl-D-propargyl-glycinyl)-4-(1-methylpiperidin-4-yl)piperazine (96%).
$[\alpha]^{25}_D$ –19.1°(c 0.295, Methanol)
Melting Point=115-135° C. with decomposition.
$^1$H NMR (CD$_3$OD).
APCI-MS, m/e=473 ($C_{24}H_{29}ClN_4O_2S$+1).
TLC $R_f$=0.53 (3:2 CH$_2$Cl$_2$:CMA)

Analysis for $C_{24}H_{29}ClN_4O_2S \cdot HCl \cdot 0.9H_2O$: Calcd: C, 54.83; H, 6.01; N, 10.66; Cl, 13.49. Found: C, 54.66; H, 6.06; N, 10.54; Cl, 13.75.

HPLC Analysis (Method A): >99% $t_r$=13.2 min.

EXAMPLE 53

1-(Indole-6-carbonyl-D-allylglycinyl)-4-(1-methylpiperidin-4-yl)piperazine

Using methods substantially equivalent to those described in Method D-1, the titled compound is prepared from 1-(D-allylglycinyl)-4-(1-methylpiperidin-4-yl)piperazine and indole-6-carboxylic acid (62%).

$^1$H NMR (CDCl$_3$).
APCI-MS, m/e 424 ($C_{24}H_{33}N_5O_2$+1).

Example 54

1-(Indole-6-carbonyl-D-allylglycinyl)-4-(1-methylpiperidin-4-yl)piperazine Hydrochloride Using methods substantially equivalent to those described in Salt Formation Method 3, the titled compound is prepared from 1-(indole-6-carbonyl-D-allylglycinyl)-4-(1-methylpiperidin-4-yl)piperazine (86%).

$[\alpha]^{25}_D$ –58.7° (c 0.25, Methanol)
Melting Point=110-115° C. with decomposition.
$^1$H NMR (CD$_3$OD).
APCI-MS, m/e 424 ($C_{24}H_{33}N_5O_2$+1).
TLC $R_f$=0.58 (3:7 CH$_2$Cl$_2$:CMA).
Analysis for $C_{24}H_{33}N_5O_2 \cdot 1.2HCl \cdot 1.5H_2O$: Calcd: C, 58.31; H, 7.58; N, 14.17; Cl, 8.61. Found: C, 58.35; H, 7.67; N, 14.07; Cl, 8.33.

HPLC Analysis (Method A): >99% $t_r$=10.9 min.

EXAMPLE 55

1-(6-Chlorobenzo[b]thiophene-2-carbonyl-D-allylglycinyl)-4-(1-methylpiperidin-4-yl)piperazine Using methods substantially equivalent to those described in Method D-1, the subtitled compound is prepared from 1-(D-allylglycinyl)-4-(1-methylpiperidin-4-yl)piperazine and 6-chlorobenzo[b]thiophene-2-carboxylic acid (46%).

$^1$H NMR (CDCl$_3$).
APCI-MS, m/e 475 ($C_{24}H_{31}ClN_4O_2S$+1).

EXAMPLE 56

1-(6-Chlorobenzo[b]thiophene-2-carbonyl-D-allylglycinyl)-4-(1-methylpiperidin-4-yl)piperazine Hydrochloride Using methods substantially equivalent to those described in Salt Formation Method 3, the titled compound is prepared from 1-(6-chlorobenzo[b]thiophene-2-carbonyl-D-allylglycinyl)-4-(1-methylpiperidin-4-yl)piperazine (84%).

$[\alpha]^{25}_D$ –48.5° (c 0.25, Methanol).
Melting Point=130-135° C. with decomposition.
$^1$H NMR (CD$_3$OD).
APCI-MS, m/e 475 ($C_{24}H_{31}ClN_4O_2S$+1).
TLC $R_f$=0.67 (3:7 CH$_2$Cl$_2$:CMA).
Analysis for $C_{24}H_{31}ClN_4O_2S \cdot 0.9HCl \cdot 0.9H_2O$: Calcd: C, 55.00; H, 6.48; N, 10.69; Cl, 12.85; S, 6.12. Found: C, 55.00; H, 6.46; N, 10.46; Cl, 12.74; S, 5.88.

HPLC Analysis (Method A): >99% $t_r$=13.6 min.

EXAMPLE 57

1-(5-Chloroindole-2-carbonyl-D-allylglycinyl)-4-(1-methyl-piperidin-4-yl)piperazine Using methods substantially equivalent to those described in Method D-1, the titled compound is prepared from 1-(D-allylglycinyl)-4-(1-methylpiperidin-4-yl)piperazine and 5-chloroindole-2-carboxylic acid (73%).

$^1$H NMR (CDCl$_3$).
APCI-MS, m/e 458 ($C_{24}H_{32}ClN_5O_2$+1).

EXAMPLE 58

1-(5-Chloroindole-2-carbonyl-D-allylglycinyl)-4-(1-methyl-piperidin-4-yl)piperazine Hydrochloride Using methods substantially equivalent to those described in Salt Formation Method 3, the subtitled compound is prepared from 1-(5-chloroindole-2-carbonyl-D-allylglycinyl)-4-(1-methyl-piperidin-4-yl)piperazine (82%).

$[\alpha]^{25}_D$ –60.1° (c 0.25, Methanol)
Melting Point=170-175° C. with decomposition.
$^1$H NMR (CD$_3$OD).
APCI-MS, m/e 458 ($C_{24}H_{32}ClN_5O_2$+1).
TLC $R_f$=0.57 (3:7 CH$_2$Cl$_2$:CMA).
Analysis for $C_{24}H_{32}ClN_5O_2 \cdot 1.1HCl \cdot 0.8H_2O$: Calcd: C, 56.24; H, 6.82; N, 13.66; Cl, 14.53. Found: C, 56.33; H, 7.01; N, 13.43; Cl, 14.49.

HPLC Analysis (Method A): 99% $t_r$=13.1 min.

Enzyme Inhibition assays

The ability of a test compound to inhibit factor Xa may be evaluated in one or more of the following Enzyme Inhibition assays, or in other standard assays known to those skilled in the art.

Enzyme Inhibition Assay

Human factor Xa and human thrombin are purchased from Enzyme Research Laboratories (South Bend, Ind., USA). Other proteases are from other commercial sources. Chromogenic para-nitroanilide peptide protease substrates are purchased from Midwest Biotech (Fishers, Ind., USA).

The binding affinities for human factor Xa are were measured as apparent association constants (Kass) derived from protease inhibition kinetics as described previously.[a,b,c,d] The apparent Kass values are obtained using automated (BioMek-1000) dilutions of inhibitors (Kass determinations are performed in triplicate at each of four-eight inhibitor concentrations) into 96-well plates and chromogenic substrate hydrolysis rates determined at 405 nm using a Thermomax plate reader from Molecular Devices (San Francisco). For factor Xa inhibition, the assay protocol is: 50 μL buffer (0.06 M tris, 0.3 M NaCl, pH 7.4); 25 μL inhibitor test solution (in MeOH); 25 μL human factor Xa (32 nM in 0.03 M tris, 0.15 M NaCl, 1 mg/mL HSA); finally, 150 μL BzIleGluGlyArgpNA (0.3 mM in water) added within 2 min to start hydrolysis. Final [factor Xa] is 3.2 nM. [Free Xa] and [bound Xa] are determined from linear standard curves on the same plate by use of SoftmaxPro software for each inhibitor concentration and apparent Kass calculated for each inhibitor concentration which produced hydrolysis inhibition between 20% and 80% of the control (3.2 nM factor Xa): apparent Kass [E:I]/[E$_f$][I$_f$]=[E$_b$]/[E$_f$][I°–I$_b$]. The apparent Kass values so obtained are approximately the inverse of the Ki for the respective inhibitors [1/appKass=app Ki]. The variability of mean apparent Kass values determined at the single substrate concentration is +/−15%. The assay system Km was measured as 0.347+/−0.031 mM [n=4]; and Vmax was 13.11+/−0.76 μM/min.

Kass values are determined with thrombin and other proteases using the same protocol with the following enzyme and substrate concentrations:
thrombin, 5.9 nM with 0.2 mM BzPheValArgpNA;
factor XIa, 1.2 nM with 0.4 mM pyroGluProArgpNA;
factor XIIa, 10 nM with 0.2 mM HDProPheArgpNA;
plasmin, 3.4 nM with 0.5 mM HDValLeuLyspNA;
nt-PA, 1.2 nM with 0.8 mM HDIleProArgpNA;
urokinase, 0.4 nM with 0.4 mM pyroGluGlyArgpNA;
aPC, 3 nM with 0.174 mM pyroGluProArgpNA;
plasma kallikrein, 1.9 nM with D-ProPheArgpNA; and
bovine trypsin, 1.4 nM with 0.18 mM BzPheValArgpNA.

Citations
(a) Sall D J, J A Bastian, S L Briggs, J A Buben, N Y Chirgadze, D K Clawson, M L Denny, D D Giera, D S Gifford-Moore, R W Harper, K L Hauser, V J Klimkowski, T J Kohn, H-S Lin, J R McCowan, A D Palkowitz, G F Smith, M E Richett, K Takeuchi, K J Thrasher, J M Tinsley, B G Utterback, S-CB Yan, M Zhang. Dibasic Benzo[b]thiophenes Derivatives as a Novel Class of Active Site Directed Thrombin Inhibitors. 1. Determination of the Serine Protease Selectivity, Structure-Activity Relationships and Binding Orientation. J Med Chem 40 3489-3493 (1997).
(b) Smith G F, T J Craft, D S Gifford-Moore, W J Coffman, K D Kurz, E Roberts, R T Shuman, G E Sandusky, N D Jones, N Chirgadze, and C V Jackson. A Family of Arginal Thrombin Inhibitors Related to Efegatran. Sem. Thrombos. Hemost. 22, 173-183 (1996).
(c) Smith G F, D S Gifford-Moore, T J Craft, N Chirgadze, K J Ruterbories, T D Lindstrom, J H Satterwhite. Efegatran: A New Cardiovascular Anticoagulant. In New Anticoagulants for the Cardiovascular Patient. Ed. R Pifarre. Hanley & Belfus, Inc., Philadelphia (1997) pp 265-300.
(d) Sall D J, D L Bailey, J A Bastian, N Y Chirgadze, A C Clemens-Smith, M L Denney, M J Fisher, D D Geira, D S Gifford-Moore, R W Harper, L M Johnson, V J Klimkowski, T J Kohn, H S Lin, J R McCowan, A D Palkowitz, M E Richett, G F Smith, D W Snyder, K Takeuchi, J E Toth, M Zang. Diamino Benzo[b]thiophene Derivatives as a Novel Class of Active Site Directed Thrombin Inhibitors: 5. Potency, Efficacy and Pharmacokinetic Properties of Modified C-3 Side Chain Derivatives. J. Med. Chem., 43, 649-663 (2000).

The compounds of formula (I) exemplified herein have been found to exhibit a Kass of greater than $1 \times 10^6$ L/mole in the enzyme inhibition assay. For example, the compounds, or their pharmaceutically acceptable salts, listed hereinabove as preferred and exemplified in Examples 6, 9 and 18 have been to exhibit Kass values of about 20, 89 and $358 \times 10^6$ L/mole, respectively.

The ability of a test compound to elongate Partial Thromboplastin Time (Prothrombin Time) may be evaluated in the following test protocols.

Partial Thromboplastin Time (Prothrombin) Test Protocol

Venous blood is collected into 3.2% (0.109 M) trisodium citrate vacutainer tubes at 1 volume of anticoagulant to nine volumes of blood. The blood cells are separated by centrifugation at 700 g for ten minutes to yield plasma, which is frozen at 70° C. until required.

To perform the test, 100 μL of plasma are pipetted into in a glass test tube, 1 μL of test compound in DMSO is added, and allowed to warm to 37° over two minutes. 100 μL of warm (37°) Manchester (tissue thromboplasin) reagent (Helena Biosciences, UK) is added, allowed to equilibrate for two minutes. 100 μL of warm (37° C.) 25 mM calcium chloride solution is added to initiate clotting. The test tube is tilted three times through a 900 angle every five seconds to mix the reagents and the time to clot formation recorded. Data from a series of observations and test compound concentrations are analysed by a SAS statistical analysis program and a CT2 (Concentration required to double clotting time) for each compound is generated.

The compound of the invention has been found to significantly elongate the partial thromboplastin time (Prothrombin time).

Alternative Prothrombin Time and APTT Protocols

Coagulation Determinations: Prothrombin Times and APTT values are determined in HUMAN PLASMA with a STA instrument (Stago). BioPT is a special non-plasma clotting assay triggered with human tissue factor (Innovin). Possible binding to albumen or to lipid are assessed by comparing the BioPT effects in the presence/absence of 30 mg/mL human albumen (HSA) and 1 mg/mL phosphatidyl choline (PC). Inhibitors are delivered in 50% aqueous methanol vehicle.

APTT ASSAY

75 μL plasma Citrol Baxter-Dade Citrated Normal Human Plasma

25 μL test solution

75 μL Actin Baxter-Dade Activated Cephaloplastin incubate 2 min min. @ 37° C.

75 μl CaCl$_2$ (0.02 M)

PT ASSAY

75 μL plasma

25 μL test solution

75 μL saline incubate 1 min. @ 37° C.

75 μL Innovin Baxter-Dade Recombinant Human Tissue Factor

The invention claimed is:
1. A compound of formula (I)

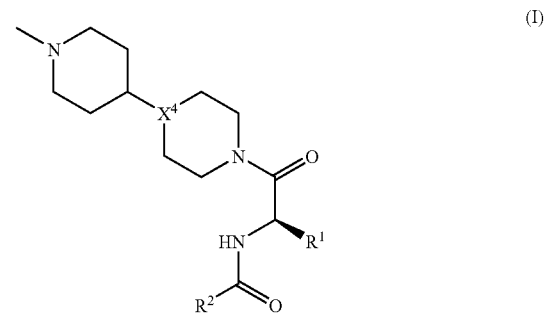

in which
R$^1$ represents (1-4C)alkyl, (2-4C)alkenyl or (2-4C)alkynyl; and
R$^2$ is selected from

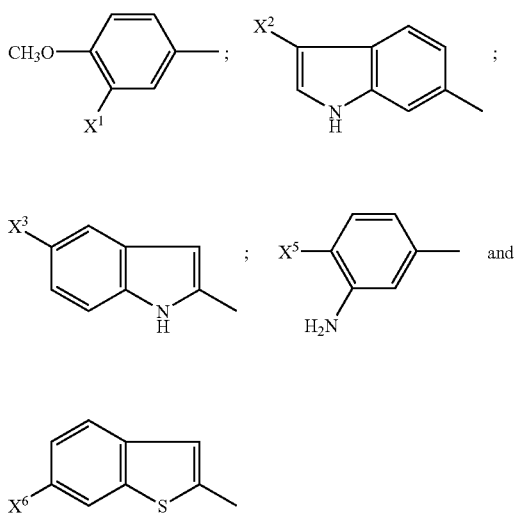

in which
X¹ represents a hydrogen atom or a halogen atom;
X² represents a hydrogen atom, a methyl group, a chlorine atom or a bromine atom;
X³ represents a hydrogen atom, a methyl group or a halogen atom;
X⁵ represents chloro, methoxy or methyl;
X⁶ represents a hydrogen atom, a halogen atom or a methyl group; and
X⁴ represents N;
or a pharmaceutically acceptable salt thereof.

2. A compound as claimed in claim 1, in which $R^2$ is selected from

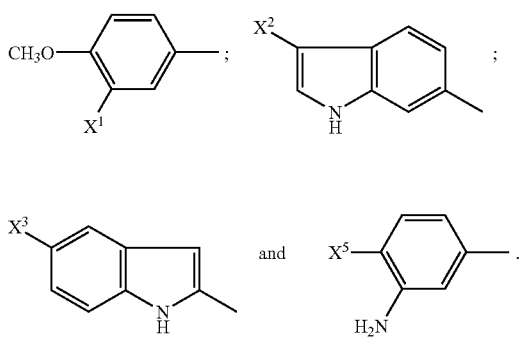

3. A compound as claimed in claim 2, in which $R^2$ is selected from

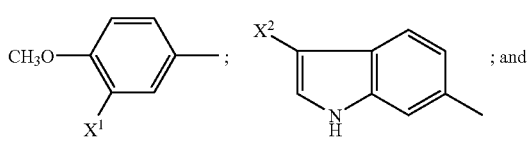

-continued

4. A compound as claimed in claim 1, in which $R^2$ is selected from

5. A compound as claimed in claim 1, in which $R^1$ is a (1-4C)alkyl group.

6. A compound as claimed in claim 3, in which $R^1$ is methyl, ethyl, propyl, 2-propyl, butyl, t-butyl, 1-methylpropyl or 2-methylpropyl.

7. A compound as claimed in claim 6, in which $R^1$ is 2-propyl.

8. A compound as claimed in claim 1, in which $R^1$ is methyl, ethyl, propyl, 2-propyl, butyl, t-butyl, 1-methylpropyl, 2-methylpropyl, prop-2-enyl or prop-2-ynyl.

9. A compound as claimed in claim 1, in which
X¹ represents a hydrogen atom or a fluorine atom;
X² represents a hydrogen atom or a chlorine atom;
X³ represents a fluorine or chlorine atom; and
X⁶ represents a chlorine atom.

10. A compound as claimed in claim 9, in which $R^2$ is 4-methoxyphenyl, indol-6-yl, 3-methylindol-6-yl, 3-chloroindol-6-yl, 5-chloroindol-2-yl, 3-fluoro-4-methoxyphenyl, 5-fluoroindol-2-yl or 6-chlorobenzo[b]thiophen-2-yl.

11. A compound as claimed in claim 3, in which
X¹ represents a hydrogen atom or a fluorine atom;
X² represents a hydrogen atom or a chlorine atom; and
X³ represents a chlorine atom.

12. A compound as claimed in claim 11, in which $R^2$ is 4-methoxyphenyl, indol-6-yl, 3-methylindol-6-yl, 3-chloroindol-6-yl, or 5-chloroindol-2-yl.

13. A compound as claimed in claim 11, in which $R^2$ is 4-methoxyphenyl, indol-6-yl or 5-chloroindol-2-yl.

14. A compound as claimed in claim 1, which is selected from:
1-(5-chloroindole-2-carbonyl-D-valinyl)-4-(1-methylpiperidin-4-yl)piperazine, and pharmaceutically acceptable salts thereof.

15. A process for preparing a compound as claimed in claim 1, which comprises (a) reacting a compound of formula (II)

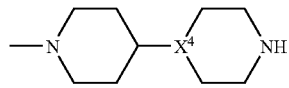

(II)

or a salt thereof, with a compound of formula (III)

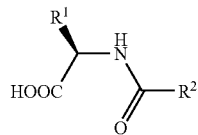

(III)

or a reactive derivative thereof; or (b) reacting a compound of formula (IV)

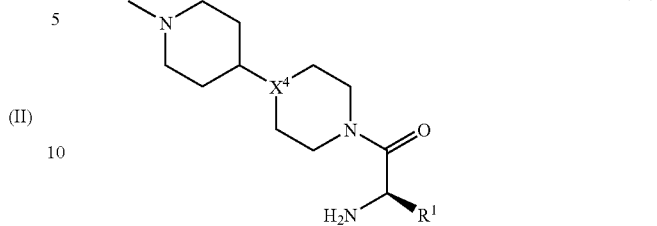

(IV)

or a salt thereof, with a compound of formula (V)

(V)

or a reactive derivative thereof;
followed, if a pharmaceutically acceptable salt is desired, by forming a pharmaceutically acceptable salt.

16. A pharmaceutical composition, which comprises a compound as claimed in claim 1, together with a pharmaceutically acceptable diluent or carrier.

17. A method of treating a thrombotic disorder in a subject requiring treatment, which comprises administering to said subject an effective amount of a compound as claimed in claim 1.

* * * * *